United States Patent [19]

Gardella et al.

[11] Patent Number: 6,147,186
[45] Date of Patent: Nov. 14, 2000

[54] PARATHYROID HORMONE-RELATED PEPTIDE ANALOGS

[75] Inventors: Thomas J. Gardella, Needham; Harald Jüppner, Boston, both of Mass.

[73] Assignee: The General Hospital Corporation, Boston, Mass.

[21] Appl. No.: 08/903,497

[22] Filed: Jul. 30, 1997

Related U.S. Application Data

[60] Provisional application No. 60/025,471, Jul. 31, 1996, abandoned.

[51] Int. Cl.$^7$ .................................................. C07K 14/635
[52] U.S. Cl. .............................. 530/324; 530/300; 514/12
[58] Field of Search .............................. 514/12; 530/324, 530/300

[56] References Cited

U.S. PATENT DOCUMENTS

5,589,452   12/1996   Krstenansky .............................. 514/12

FOREIGN PATENT DOCUMENTS

| 0 341 962 A2 | 11/1989 | European Pat. Off. . |
| WO 92/17602 | 10/1992 | WIPO . |
| WO 95/02610 | 1/1995 | WIPO . |
| WO 96/03437 A1 | 2/1996 | WIPO . |

OTHER PUBLICATIONS

Abdul–Bedi et al., Endocrinology, vol. 125, No. 4, 2215–2217, 1989.

Abou–Samra, A.-B., et al., "Non–Homologous Sequences of Parathyroid Hormone and the Parathyroid Hormone Related Peptide Bind to a Common Receptor on ROS 17/2.8 Cells," *Endocrinology* 125(4):2215–2217 (1989).

Abou–Samra, A.-B., et al., "Expression cloning of a common receptor for parathyroid hormone and parathyroid hormone–related pepetide from rat osteoblast–like cells: A single receptor stimulates intracellular accumulation of both cAMP and inositol trisphosphates and increases intracellular free calcium," *Proc. Natl. Acad. Sci. USA* 89:2732–2736 (1992).

Barden, J.A., and Kemp, B.E., "NMR study of a 34–residue N–terminal fragment of the parathyroid–hormone–related protein secreted during humoral hypercalcemia of malignancy," *Eur. J. Biochem.* 184:379–394 (1989).

Barden, J.A., and Kemp, B.E., "NMR Solution Structure of Human Parathyroid Hormone(1–34)," *Biochemistry* 32:7126–7132 (1993).

Broadus, A.E., and Stewart, A.F., "Parathyroid Hormone–Related Protein: Structure, Processing, and Physiological Actions," *The Parathyroids: Basic and Clinical Concepts*, Bilezikian, J.P., et al., Eds., Raven Press; New York, pp. 259–294 (1994).

Bundi, A., et al., "Characterisation of a Local Structure in the Synthetic Parathyroid Hormone Fragment 1–34 by $^1$H Nuclear–Magnetic–Resonance Techniques," *Eur. J. Biochem.* 91:201–208 (1978).

Caulfield, M.P., et al., "The Bovine Renal Parathyroid Hormone (PTH) Receptor Has Equal Affinity for Two Different Amino Acid Sequences: The Receptor Binding Domains of PTH and PTH–Related Protein Are Located within the 14–34 Region," *Endocrinology* 127(1):83–87 (1990).

Caulfield, M.P., and Rosenblatt, M., "Parathyroid Hormone–Receptor Interactions," *Trends Endocrinol. Metabolism* 1(3):164–168 (1990).

Chorev, M., et al., "Modifications of Position 12 in Parathyroid Hormone and Parathyroid Hormone Related Protein: Toward the Design of Highly Potent Antagonists," *Biochemistry* 29(6):1580–1586 (1990).

Gardella, T.J., et al., "Scanning mutagenesis of the 23–35 region of parathyroid hormone reveals important determinants of receptor binding," in: *Calcium Regulating Hormones and Bone Metabolism: Basic and clinical aspects*, vol. 11, Cohn, D.V., et al., Eds., Excerpta Medica; Amsterdam, pp. 218–222 (1992).

Gardella, T.J., et al., "Parathyroid Hormone (PTH)–PTH–related Peptide Hybrid Peptides Reveal Functional Interactions between the 1–14 and 15–34 Domains of the Ligand," *J. Biol. Chem.* 270(12):6584–6588 (Mar. 1995).

Gardella, T.J., et al., "Converting Parathyroid Hormone–related Peptide (PTHrP) into a Potent PTH–2 Receptor Agonist," *J. Biol. Chem.* 271(33):19888–19893 (Aug. 1996).

Hrsuka, K.A., et al., "Stimulation of Inositol Trisphosphate and Diacylglycerol Production in Renal Tubular Cells by Parathyroid Hormone," *J. Clin. Invest.* 79:230–239 (1987).

Ishihara, T., et al., "Molecular cloning and expression of a cDNA encoding the secretin receptor," *EMBO J.* 10(7):1635–1641 (1991).

Jelinek, L.J., et al., "Expression Cloning and Signaling Properties of the Rat Glucagon Receptor," *Science* 259:1614–1616 (1993).

Jüppner, H., et al., "The Parathyroid Hormone–Like Peptide Associated with Humoral Hypercalcemia of Malignancy and Parathyroid Hormone Bind to the Same Receptor on the Plasma Membrane of ROS 17/2.8 Cells," *J. Biol. Chem.* 263(18):8557–8560 (1988).

Jüppner, H., et al., "A G Protein–Linked Receptor for Parathyroid Hormone and Parathyroid Hormone–Related Peptide," *Science* 254:1024–1026 (1991).

Karaplis, A.C., et al., "Lethal skeletal dysplasia from targeted disruption of the parathyroid hormone–related peptide gene," *Genes & Development* 8: 277–289 (1994).

(List continued on next page.)

*Primary Examiner*—F. T. Moezie
*Attorney, Agent, or Firm*—Sterne, Kessler, Goldstein & Fox PLLC

[57] ABSTRACT

The present invention relates to novel PTHrP analogs that have been converted into potent PTH-2 receptor agonists or antagonists by the substitution of one or more amino acid residues of PTHrP to the corresponding residue(s) of PTH. A method of treating various disease states associated with altered function of the PTH-2 receptor, using these PTHrP analogs, is also described.

6 Claims, 11 Drawing Sheets-

OTHER PUBLICATIONS

Klaus, W., et al., "Investigation of the Solution Structure of the Human Parathyroid Hormone Fragment (1–34) by $^1$H NMR Spectroscopy, Distance Geometry, and Molecular Dynamics Calculations," *Biochemistry* 30:6936–6942 (1991).

Kronenberg, H.M., et al., "Parathyroid Hormone: Biosynthesis, Secretion, Chemistry, and Action," in: *Physiology and Pharmacology of Bone*, Mundy, G.R., and Martin, T.J., Eds., Springer–Verlag; Berlin, pp.507–567 (1993).

Lee, C., et al., "Homolog–Scanning Mutagenesis of the Parathyroid Hormone (PTH) Receptor Reveals PTH–(1–34) Binding Determinants in the Third Extracellular Loop," *Mol. Endocrinol.* 9(10):1269–1278 (Oct. 1995).

Lin, H.Y., et al., "Expression Cloning of an Adenylate Cyclase–Coupled Calcitonin Receptor," *Science* 254:1022–1024 (1991).

Marx, U.C., et al., "Structure of Human Parathyroid Hormone 1–37 in Solution," *J. Biol. Chem.* 270(25):15194–15202 (Jun. 1995).

Nakamoto, C., et al., "Probing the Bimolecular Interactions of Parathyroid Hormone with the Human Parathyroid Hormone/Parathyroid Hormone–Related Protein Receptor. 1. Design, Synthesis and Characterization of Photoreactive Benzophenone–Containing Analogs of Parathyroid Hormone," *Biochemistry* 34:10546–10552 (Aug. 1995).

Nussbaum, S.R., et al., "Parathyroid Hormone • Renal Receptor Interactions: Demonstration of Two Receptor–Binding Domains," *J. Biol. Chem.* 255(21):10183–10187 (1980).

Nutt, R.F., et al., "Removal of Partial Agonism from Parathyroid Hormone (PTH)–Related Protein–(7–34)NH$_2$ by Substitution of PTH Amino Acids at Positions 10 and 11," *Endocrinology* 127(1):491–493 (1990).

Ray, F.R., et al., "NMR solution structure of the [Ala$^{26}$] parathyroid–hormone–related protein(1–34) expressed in humoral hypercalcemia of malignancy," *Eur. J. Biochem.* 211:205–211 (1993).

Rosenblatt, M., and Potts, J.T., Jr., "Design and Synthesis of Parathyroid Hormone Analogues of Enhanced Biological Activity," *Endo. Res. Comm.* 4(2):115–133 (1977).

Schipani, E., et al., "Identical Complementary Deoxyribonucleic Acids Encode a Human Renal and Bone Parathyroid Hormone (PTH)/PTH–Related Peptide Receptor," *Endocrinology* 132(5):2157–2165 (1993).

Shigeno, C., et al., "Parathyroid Hormone Receptors Are Plasma Membrane Glycoproteins with Asparagine–Linked Oligosaccharides," *J. Biol. Chem.* 263(8):3872–3878 (1988).

Ureña, P., et al., "Regulation of Parathyroid Hormone (PTH)/PTH–Related Peptide Receptor Messenger Ribonucleic Acid by Glucocorticoids and PTH in ROS 17/2.8 and OK Cells," *Endocrinology* 134(1):451–456 (1994).

Usdin, T.B., et al., "Identification and Functional Expression of a Receptor Selectively Recognizing Parathyroid Hormone, and PTH2 Receptor," *J. Biol. Chem.* 270(26):15455–15458 (Jun. 1995).

International Search Report for International Application No. PCT/US97/13360.

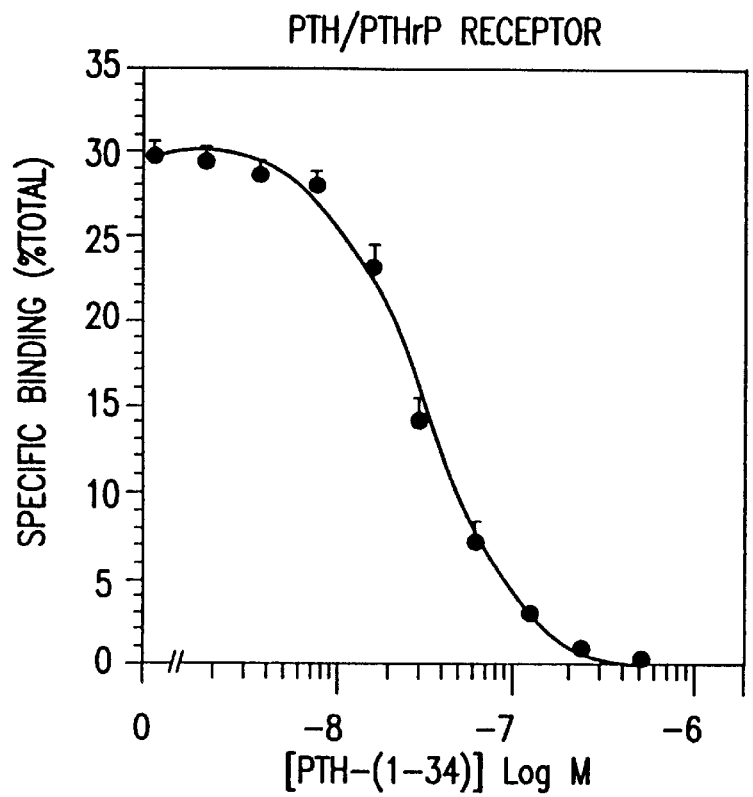
FIG.2A
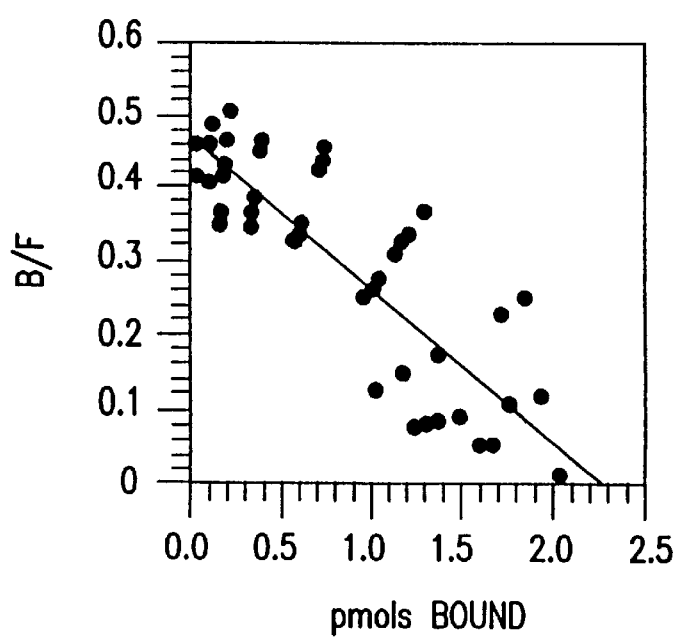
FIG.2A1

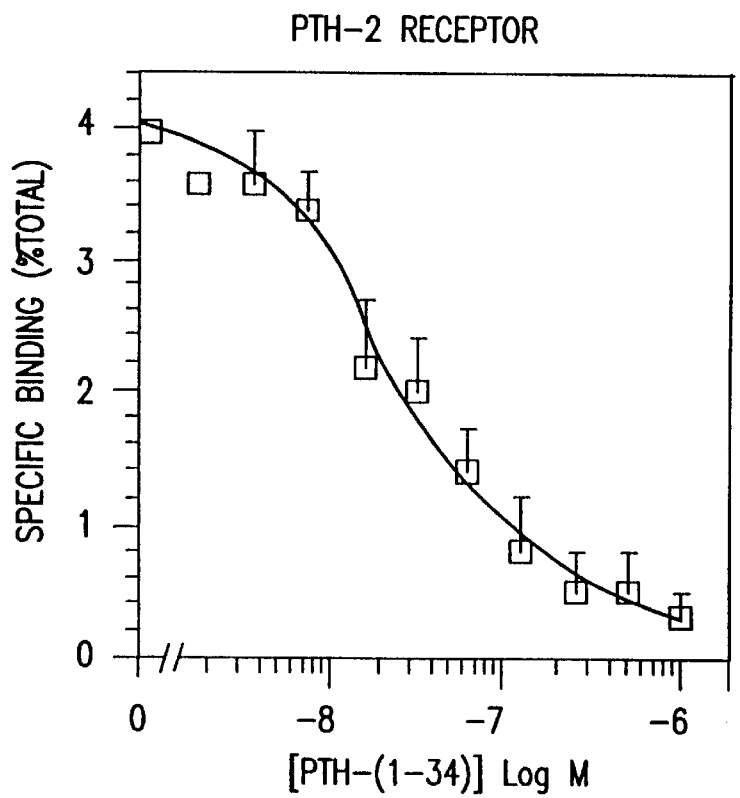
FIG.2B
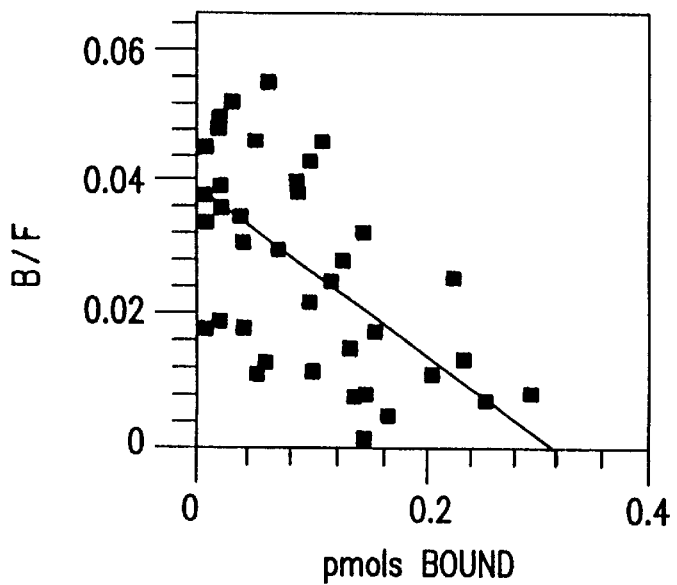
FIG.2B1

```
                                      1            5              10             15             20             25             30        34
PTH(1-34)                             S  V  S  E  I  Q  L  M  H  N  L  G  K  H  L  N  S  M  E  R  V  E  W  L  R  K  K  L  Q  D  V  H  N  Y
PTHrP(1-36)                          [A  V  S  E  H  Q  L  L  H  D  K  G  K  S  I  Q  D  L  R  R  R  F  F  L  H  H  L  I  A  E  I  H  T  A  E  Y]

Hybrid-1                                                                       14
PTHrP(1-14)/PTH(15-34)               [A  V  S  E  H  Q  L  L  H  D  K  G  K  S] L  N  S  M  E  R  V  E  W  L  R  K  K  L  Q  D  V  H  N  Y Hybrid-5                                                                                      18
PTHrP(1-18)/PTH(19-34)               [A  V  S  E  H  Q  L  L  H  D  K  G  K  S  I  Q  D  L] E  R  V  E  W  L  R  K  K  L  Q  D  V  H  N  Y Hybrid-4                                                                                                    21
PTHrP(1-21)/PTH(22-34)               [A  V  S  E  H  Q  L  L  H  D  K  G  K  S  I  Q  D  L  R  R  R] E  W  L  R  K  K  L  Q  D  V  H  N  Y Hybrid-3                                                                                                                24
PTHrP(1-23)/PTH(24-34)               [A  V  S  E  H  Q  L  L  H  D  K  G  K  S  I  Q  D  L  R  R  R  F  F] L  R  K  K  L  Q  D  V  H  N  Y Hybrid-2                                                     14
PTH(1-14)/PTHrP(15-34)                S  V  S  E  I  Q  L  M  H  N  L  G  K  H [I  Q  D  L  R  R  R  F  F  L  H  H  L  I  A  E  I  H  T  Y]
```

FIG. 3

PARATHYROID HORMONE-RELATED PEPTIDE ANALOGS

CROSS-REFERENCE TO RELATED APPLICATIONS

This application claims the benefit under 35 U.S.C. § 119(e) of U.S. Provisional Application No. 60/025,471, filed Jul. 31, 1996 now abandoned. The content of this provisional application is incorporated by reference in its entirety.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

The present invention relates to parathyroid hormone-related peptide (PTHrP) analogs. In particular, the invention relates to PTHrP analogs having one or more amino acid substitutions that confer PTH-2 receptor antagonist or agonist properties to the analog.

2. Description of Related Art

Parathyroid hormone (PTH) is a major regulator of calcium homeostasis whose principal target cells occur in bone and kidney. Regulation of calcium concentration is necessary for the normal function of the gastrointestinal, skeletal, neurologic, neuromuscular, and cardiovascular systems. PTH synthesis and release are controlled principally by the serum calcium level; a low level stimulates and a high level suppresses both hormone synthesis and release. PTH, in turn, maintains the serum calcium level by directly or indirectly promoting calcium entry into the blood at three sites of calcium exchange: gut, bone, and kidney. PTH contributes to net gastrointestinal absorption of calcium by favoring the renal synthesis of the active form of vitamin D. PTH promotes calcium resorption from bone by inhibiting osteoblasts and, indirectly, by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH exerts these effects primarily through receptor-mediated activation of adenylate cyclase, although receptor-mediated activation of phospholipase C by PTH has also been reported (Hruska et al., *J. Clin. Invest.* 79:230 (1987)).

Disruption of calcium homeostasis may produce many clinical disorders (e.g., severe bone disease, anemia, renal impairment, ulcers, myopathy, and neuropathy) and usually results from conditions that produce an alteration in the level of parathyroid hormone. Hypercalcemia is a condition that is characterized by an elevation in the serum calcium level. It is often associated with primary hyperparathyroidism in which an excess of PTH production occurs as a result of a lesion (e.g., adenoma, hyperplasia, or carcinoma) of the parathyroid glands. Another type of hypercalcemia, humoral hypercalcemia of malignancy (HHB) is the most common paraneoplastic syndrome. It appears to result in most instances from the production by tumors (e.g., squamous, renal, ovarian, or bladder carcinomas) of a novel class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells, and lactating mammary tissues. In many HHM malignancies, PTHrP is found in the circulatory system at high levels, thereby producing the elevated calcium levels associated with HHM.

The pharmacological profiles of PTH and PTHrP are nearly identical in most in vitro assay systems, and elevated blood levels of PTH (i.e., primary hyperparathyroidism) or PTHrP (i.e., HHM) have comparable effects on mineral ion homeostasis (Broadus, A. E. & Stewart, A. F., "Parathyroid hormone-related protein: Structure, processing and physiological actions," in *Basic and Clinical Concepts*, Bilzikian, J. P. et al., eds., Raven Press, New York (1994), pp. 259–294; Kronenberg, H. M. et al., "Parathyroid hormone: Biosynthesis, secretion, chemistry and action," in *Handbook of Experimental Pharmacology*, Mundy, G. R. & Martin, T. J., eds., Springer-Verlag, Heidelberg (1993), pp. 185–201). The similarities in the biological activities of the two ligands can be explained by their interaction with a common receptor, the PTH/PTHrP receptor, which is expressed abundantly in bone and kidney (Urena, P. et al., *Endocrinology* 134:451–456 (1994)).

The binding of either radiolabeled PTH-(1–34) or PTHrP-(1–36) to the PTH/PTHrP receptor is competitively inhibited by either unlabeled ligand (Jüppner, H. et al., *J. Biol. Chem.* 263:8557–8560 (1988); Nissenson, R. A. et al., *J. Biol. Chem.* 263:12866–12871 (1988)). Thus, the recognition sites for the two ligands in the PTH/PTHrP receptor probably overlap. In both PTH and PTHrP, the 15–34 region contains the principal determinants for binding to the PTH/PTHrP receptor. Although these regions show only minimal sequence homology (only 3 amino acid identities), each 15–34 peptide can block the binding of either PTH-(1–34) or PTHrP-(1–34) to the PTH/PTHrP receptor (Nussbaum, S. R. et al., *J. Biol. Chem.* 255:10183–10187 (1980); Caulfield, M. P. et al., *Endocrinology* 127:83–87 (1990); Abou-Samra, A.-B. et al., *Endocrinology* 125:2215–2217 (1989)). Further, the amino terminal portion of each ligand is required for bioactivity, and these probably interact with the PTH/PTHrP receptor in similar ways, since 8 of 13 of these residues are identical in PTH and PTHrP.

The PTH/PTHrP receptor is a member of a distinct family of G protein-coupled receptors (Jüppner, H. et al., *Science* 254:1024–1026 (1991); Abou-Samra, A. B. et al., *Proc. Natl. Acad. Sci (USA)* 89:2732–2736 (1992)) that includes receptors for other peptide hormones such as secretin (Ishihara, T. et al., *EMBO J.* 10:1635–1641 (1991)), calcitonin (Lin, H. Y. et al., *Science* 254:1022–1024 (1991)) and glucagon (Jelinek, L. J. et al., *Science* 259:1614–1616 (1993)). Using degenerate oligonucleotides corresponding to conserved regions of the PTH/secretin/calcitonin receptor family, Usdin et al. has identified a new receptor cDNA derived from rat and human brain that was most closely related to the PTH/PTHrP receptor (51% overall amino acid sequence identity) (Usdin, T. et al., *J. Biol. Chem.* 270:15455–15458 (1995)). This new receptor, the PTH-2 receptor, responded efficiently, potently, and specifically to PTH-(1–34), but interestingly, did not respond at all to PTHrP. Id. This observation implied that structural differences in the PTH and PTHrP ligands determined selectivity for interaction with the PTH-2 receptor. The PTH-2 receptor was found predominantly in the brain and pancreas. Id.

Since the PTH-2 receptor was found in brain and pancreas, it is likely to have a physiological role in the normal functioning of those organs. Diseases associated with brain and pancreatic dysfunction may in fact be explained by the altered action of the PTH-2 receptor. Such diseases could then be treated with a PTH-2 receptor selective antagonist. Other antagonists that are available are not selective and thus, are not desired because they would also antagonize the PTH/PTHrP receptor, which could have negative consequences in terms of calcium regulation and skeletal function.

Accordingly, there is a need in the art for the development of PTH-2 receptor selective agonists and antagonists: (1) to assist in further elucidating the biological role of the PTH-2 receptor; (2) to map specific sites of ligand-receptor interaction; and (3) as potential new therapeutic compositions that can be used in the treatment of disorders associated with altered action or genetic mutation of the PTH-2 receptor.

SUMMARY OF THE INVENTION

To begin to define residues involved in the ligand-specificity of the PTH-2 receptor, the inventors studied the interaction of several PTH/PTHrP hybrid ligands and other related peptide analogs, with the human PTH-2 receptor. The results showed that two sites in PTH and PTHrP fully account for the different potencies that the two ligands exhibited with PTH-2 receptors; residue 5 (His in PTHrP and Ile in PTH) determined signaling capability, while residue 23 (Phe in PTHRP and Trp in PTH) determined binding affinity. By changing these two residues of PTHrP (i.e., residue 5 and 23) to the corresponding residues of PTH, the inventors were able to convert PTHrP into a ligand that avidly bound to the PTH-2 receptor, and fully and potently stimulated cAMP formation. Changing residue 23 alone yielded [$Trp^{23}$]hPTHrP-(1–36), which was an antagonist for the PTH-2 receptor, but a full agonist for the PTH/PTHrP receptor. Accordingly, the inventors concluded that residues 5 and 23 in PTH and PTHrP play key roles in signaling and binding interactions, respectively, with the PTH-2 receptor.

Thus, in accordance with one aspect of the present invention, there is provided a novel PTHrP analog that is a potent PTH-2 receptor agonist, as well as a potent PTH/PTHrP receptor agonist. In a preferred embodiment, PTHrP analog is altered at residues 5 and 23 to the corresponding residues of PTH. Most preferably, the invention includes PTHrP analogs having an amino acid substitution of histidine for isoleucine at position 5 of PTHrP, as well as phenylalanine for tryptophan at position 23 of PTHrP. In a particular embodiment, the PTHrP analog is [$Ile^5$, $Trp^{23}$]PTHrP-(1–36).

In accordance with another aspect of the present invention, there is provided a novel PTHrP analog that is a potent PTH-2 receptor selective antagonist. In a preferred embodiment, the analog is altered at PTHrP residue 23 to the corresponding residue of PTH. Most preferably, the invention includes PTHrP analogs having a single amino acid substitution of phenylalanine for tryptophan at position 23 of PTHrP. In a particular embodiment, the PTHrP analog is [$Trp^{23}$]PTHrP-(1–36).

In accordance with yet a further aspect of the invention, there is provided a method for treating a medical disorder that results from altered or excessive action of the PTH-2 receptor, comprising administering to a patient a therapeutically efficient amount of a PTHrP analog, sufficient to inhibit activation of the PTH-2 receptor of said patient. In a preferred embodiment, the PTHrP analog used in the method has a single amino acid substitution of phenylalanine for tryptophan at position 23 of PTHrP. In a particular embodiment, the PTHrP analog is [$Trp^{23}$]PTHrP-(1–36).

In accordance with yet a further aspect of the invention, there is provided a method for treating osteoporosis, comprising administering to a patient a therapeutically efficient amount of a PTHrP analog, sufficient to activate the PTH/PTHrP receptor and PTH-2 receptor of said patient. In a preferred embodiment, the PTHrP analog used in the method has an amino acid substitution of histidine for isoleucine at position 5 of PTHrP, as well as phenylalanine for tryptophan at position 23 of PTHrP. In a particular embodiment, the PTHrP analog is [$Ile^5$, $Trp^{23}$]PTHrP-(1–36).

In addition, any other amino-acid substitutions at positions 5 and/or 23, which do not destroy the ability of the PTHrP analog to antagonize or agonize the PTH-2 receptor (as determined by assays known to the skilled artisan and discussed below), are included within the scope of the present invention.

BRIEF DESCRIPTION OF THE FIGURES

FIG. 2 depicts a scatchard analysis of PTH-(1–34) binding to PTH/PTHrP or PTH-2 receptors. COS-7 cells transfected with plasmid DNA (200 ng/well) encoding either the human PTH/PTHrP receptor (FIG. 2A) or human PTH-2 receptor (FIG. 2B) were evaluated in competition-binding studies performed for six hours at 4° C. The radioligand was $^{125}$I-[NleTyr$^{8,21}$,Tyr$^{34}$]rPTH-(1–34)amide (100,000 CPM/well), as a tracer, and the competitor ligand was the same unlabeled peptide. Data are the mean (±s.e.m.) of four experiments, each performed in duplicate. The insets show Scatchard plots of the individual data points from the linear portions of each experiment. The mean dissociation constants (kds) and B$_{max}$ values, as receptors/cell, derived from these experiments are shown above the panel s. Statistical analysis indicated that the surface densities of the two receptors, but not the Kd values, differed significantly (p values=0.0003, and 0.14, respectively, students t test).

FIG. 3 depicts the primary structures of PTH, PTHrP and hybrid ligands (Seq ID NOS:1–7). The biologically active regions of PTH, PTHrP, and the PTH/PTHrP hybrid ligands used in this study are shown. Sequences corresponding to PTHrP are shaded. All peptides contained the carboxy-terminal modification of tyrosine-amide, and otherwise corresponded to the native human PTH or human PTHrP sequence.

Figure 1A:
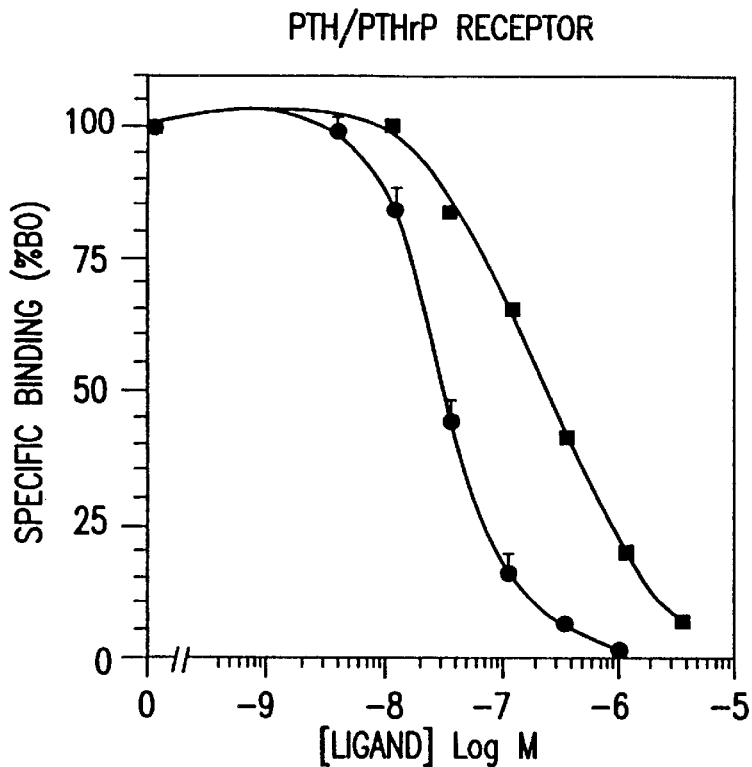
FIG. 1 depicts ligand-binding and cAMP-signaling profiles of PTH/PTHrP and PTH-2 receptors. COS-7 cells transfected with human PTH/PTHrP receptors (FIGS. 1A and 1C) or human PTH-2 receptors (FIGS. 1B and 1D) were evaluated for inhibition of radioligand binding (FIGS. 1A and 1B), or ligand-induced cAMP accumulation (FIGS. 1C and 1D). Binding studies were performed at room temperature (RT) for 2 hours. $^{125}$I-[NleTyr$^{8,21}$,Tyr$^{34}$]rPTH-(1–34)NH$_2$ (100,000 CPM/well) was used as radioligand and varying amounts of unlabeled [Tyr$^{34}$]hPTH-(1–34)NH$_2$ (●) or [Tyr$^{36}$]hPTHrP-(1–36)NH$_2$ (■) were used as competitor ligands. Symbols are indicated in the figure key. The maximum amount of tracer that specifically bound to PTH/PTHrP and PTH-2 receptors in the absence of competitor (B$_0$) was ~25% and ~5% of total radioactivity added, respectively. For cAMP stimulation assays, cells were treated with ligand for 1 hour at room temperature in the presence of IBMX. Symbols in FIGS. 1C and 1D are the same as in FIGS. 1A and 1B. Data are the mean (±s.e.m.) of 3–10 experiments, each performed in duplicate.
Figure 1B:
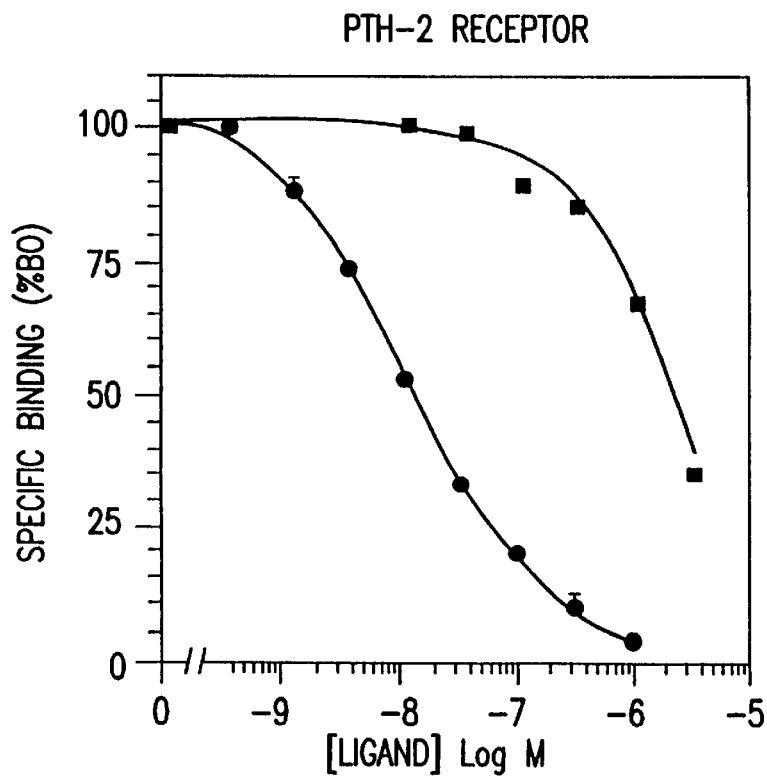

It is of interest to note that these hybrid ligands, as well as [H5]PTH-(1–34), competed very poorly for binding to the PTH/PTHrP receptor, yet efficiently stimulated cAMP formation (Table 1). The inventors have found that radioiodinated hybrid-5 peptide binds efficiently to the PTH/PTHrP receptor in COS-7 cells (specific binding ~8% of total radioactivity added. It thus appears that these altered ligands bind to the PTH/PTHrP receptor, but at a site that does not fully overlap with that used by $^{125}$I-[NleTyr$^{8,21}$,Tyr$^{34}$]rPTH-(1–34)NH$_2$.

TABLE 1

Receptor-binding properties of PTH and PTHrP analogs
COS-7 cells transfected with plasmids encoding the human PTH/PTHrP receptor or the human PTH-2 receptor were evaluated in competition binding studies that used [Nle$^{8,21}$, Y$^{34}$]rPTH-(1–34)NH$_2$ as radioligand and the indicated unlabeled ligands as competitors. Assays were performed for 2 hours at room temperature. Data are the mean (±s.e.m.) of IC$_{50}$ values obtained from the number of experiments indicated (n).

| | Binding IC50 (nM) | | | |
|---|---|---|---|---|
| Ligand | PTH/PTHrP receptor | (n) | PTH-2 receptor | (n) |
| [Nle8, 21, Y34]rPTH-(1–34)NH2 (SEQ ID NO: 1) | 58 ± 4 | 5 | 11 ± 2 | 5 |
| [Y34]hPTH-(1–34)NH2 | 39 ± 4 | 7 | 16 ± 4 | 7 |
| [Y36]hPTHrP-(1–36)NH2 (SEQ ID NO: 2) | 285 ± 47 | 10 | 2,140 ± 250 | 10 |
| Hybrid-1 (SEQ ID NO: 3) hPTHrP-(1–14)/[Y34]hPTH-(15–34)NH2 | 7,900 ± 370 | 4 | 606 ± 96 | 4 |

| | cAMP accumulation | | | |
|---|---|---|---|---|
| | PTH/PTHrP receptor | | PTH-2 receptor | |
| Ligand | EC50 (nM) | Maximum (pmoles/well) | EC50 (nM) | Maximum (pmoles/well) |
| [Y34]hPTHrP-(1–23)/hPTH-(24–34)NH2 | 0.42 ± 0.13 | 95 ± 9 | 4 >1000 | 11 ± 1 | 4 |
| Hybrid-1 (SEQ ID NO: 7) [Y34]hPTH-(1–14)/hPTHrP-(15–34)NH2 | 0.74 ± 0.37 | 123 ± 28 | 3 2.1 ± 0.5 | 58 ± 12 | 3 |

TABLE 1-continued

Receptor-binding properties of PTH and PTHrP analogs
COS-7 cells transfected with plasmids encoding the human PTH/PTHrP receptor or
the human PTH-2 receptor were evaluated in competition binding studies that used
[Nle$^{8,21}$, Y$^{34}$]rPTH-(1–34)NH$_2$ as radioligand and the
indicated unlabeled ligands as competitors. Assays were performed for 2 hours at
room temperature. Data are the mean (±s.e.m.) of IC$_{50}$ values obtained from
the number of experiments indicated (n).

| Ligand | Binding IC50 (nM) | | | |
|---|---|---|---|---|
| | PTH/PTHrP receptor | (n) | PTH-2 receptor | (n) |
| Hybrid-5 (SEQ ID NO: 4) hPTHrP-(1–18)/[Y34]hPTH-(19–34)NH2 | 4,970 ± 1,560 | 4 | 500 ± 62 | 4 |
| Hybrid-4 (SEQ ID NO: 5) hPTHrP-(1–21)/[Y34]hPTH-(22–34)NH2 | 19 ± 6 | 4 | 11 ± 3 | 4 |
| Hybrid-3 (SEQ ID NO: 6) hPTHrP-(1–23)/[Y34]hPTH-(24–34)NH2 | 1,000 ± 471 | 4 | 6,050 ± 990 | 4 |
| Hybrid-2 (SEQ ID NO: 7) hPTH-(1–14)/[Y34]hPTHrP-(15–34)NH2 | 497 ± 144 | 4 | 750 ± 210 | 4 |
| [Y36]hPTHrP-(15–36)NH2 | >10,000 | 4 | 4,970 ± 970 | 4 |
| [W23, Y36]hPTHrP-(15–36)NH2 | >10,000 | 4 | 370 ± 100 | 4 |
| [E22, W23, Y36]hPTHrP-(15–36)NH2 | >10,000 | 4 | 137 ± 36 | 4 |
| [Y34]hPTH-(15–34)NH2 | >10,000 | 3 | 624 ± 116 | 3 |
| [F23, Y34]hPTH-(15–34)NH2 | >10,000 | 4 | >10,000 | 4 |
| [W23, Y36]hpTHrP-(1–36)NH2 | 47 ± 8 | 5 | 30 ± 7 | 5 |
| [I5, Y36]hPTHrP-(1–36)NH2 | 41 ± 11 | 6 | 695 ± 171 | 6 |
| [I5, W23, Y36]hPTHrP-(1–36)NH2 | 16 ± 3 | 5 | 10 ± 1 | 5 |
| [F23, Y34]hPTH-(1–34)NH2 | 95 ± 11 | 4 | 453 ± 53 | 4 |
| [H5, Y34]hPTH-(1–34)NH2 | 5,100 ± 1,000 | 4 | 249 ± 18 | 4 |
| [H5, F23, Y34]hPTH-(1–34)NH2 | >10,000 | 3 | >10,000 | 3 |

DETAILED DESCRIPTION OF THE PREFERRED EMBODIMENTS

Previously, the present inventors had prepared a series of PTH/PTHrP hybrid ligands for the purpose of investigating whether homologous domains of PTH and PTHrP could be interchanged (Gardella, T. J. et al., J. Biol. Chem. 270:6584–6588 (1995)). The present inventors have now used these hybrid ligands and derivative peptide analogs to map regions of PTH and PTHrP that contribute to the ligand selectivity of the PTH-2 receptor. These efforts have led to the identification of two residues in the ligands that play major roles in determining the efficiency of binding and signaling interactions with the PTH-2 receptor.

The present invention provides a novel PTHrP analog that is a potent PTH-2 receptor agonist, as well as a potent PTH/PTHrP receptor agonist. In a preferred embodiment, the PTHrP analog is altered at residues 5 and 23 to the corresponding residues of PTH. Most preferably, the invention includes PTHrP analogs having an amino acid substitution of histidine for isoleucine at position 5 of PTHRP, as well as phenylalanine for tryptophan at position 23 of PTHrP. In a particular embodiment, the PTHrP analog is [Ile$^5$, Trp$^{23}$]PTHrP-(1–36).

In accordance with another aspect of the present invention, there is provided a novel PTHrP analog that is a potent PTH-2 receptor selective antagonist. In a preferred embodiment, the analog is altered at PTHrP residue 23 to the corresponding residue of PTH. Most preferably, the invention includes PTHrP analogs having a single amino acid substitution of phenylalanine for tryptophan at position 23 of PTHrP. In a particular embodiment, the PTHrP analog is [Trp$^{23}$]PTHrP-(1–36).

In addition, any other amino-acid substitutions of a nature, which do not destroy the ability of the PTHrP analog to antagonize or agonize the PTH-2 receptor (as determined by assays known to the skilled artisan and discussed below), are included in the scope of the present invention. The following Example is illustrative, and is not intended to be limiting.

Materials and Methods

Peptides and Reagents

The preparation and initial characterization of PTH/PTHrP hybrid ligands was described previously (Gardella, T. J. et al., J. Biol. Chem. 270:6584–6588 (1995)). [Nle$^{8,21}$, Tyr$^{34}$]rat(r)PTH(1–34)NH$_2$ was purchased from Bachem Fine Chemicals (Torrance, Calif.). The antagonist, [Leu$^{11}$, D-Trp$^{12}$]hPTHrP(7–34)NH$_2$, was purchased from Peninsula Laboratories (Belmont, Calif.). All other peptides were prepared by the biopolymer synthesis facility at Massachusetts General Hospital (Boston, Mass.) using solid-phase chemistry and F-moc protecting groups. $^{125}$I-[Nle$^{8,21}$,Tyr$^{34}$] rPTH-(1–34)NH$_2$ was prepared by chloramine-T iodination, and was HPLC-purified (Shigeno, C. et al., J. Biol. Chem. 263:3872–3878 (1988)). [$^{125}$I]-Na (2,000 Ci/mmol) was purchased from DuPont/New England Nuclear (Boston, Mass.). Dulbecco's modified Eagle's medium (DMEM), EGTA/trypsin and 100× antibiotic mixture (10,000 units/ml penicillin G and 10 mg/ml streptomycin) was from GIBCO; fetal bovine serum (FBS) was from Hyclone Laboratories (Logan, Utah).

DNA Transfection of COS-7 Cells

The cDNAs encoding the human PTH/PTHrP receptor (Schipani, E. et al., Endocrinology 132:2157–2165 (1993)) and the human PTH-2 receptor (Usdin, T. et al., J. Biol. Chem. 270:15455–15458 (1995)) were carried on the expression vectors pcDNA-1 and pcDNAI/Amp (InVitrogen, San Diego, Calif.), respectively. COS-7 cells were cultured and transfected as described previously (Lee, C. et al., Mol. Endocrinol. 9:1269–1278 (1995)). Cells were transfected in 24-well plates using plasmid DNA (200 ng/well) purified by cesium chloride/ethidium bromide gradient centrifugation. Ligand binding and cAMP accumulation assays were performed three days after transfection, by which time the cell density reached 500,000±100,000 cells/well.

Radioligand-Receptor Binding

Binding reactions were performed as described previously. Id. Each well (final volume: 300 ml) contained 26 fmole of $^{125}$I-[Nle$^{8,21}$,Tyr$^{34}$]rPTH(1–34)NH$_2$ (100,000 CPM) and various amounts (0.4–300 pmole) of an unlabeled competitor ligand, both diluted in binding buffer (50 mM Tris-HCl, pH 7.7, 100 mM NaCl, 5 mM KCl, 2 mM CaCl, 5% heat-inactivated horse serum, 0.5% heat-inactivated fetal bovine serum). Incubations were at room temperature for 2 hours, except for experiments involving Scatchard analysis, which were performed at 4° C. for 6 hours. At the end of the binding reaction, the cells were rinsed 3 times with 0.5 ml of binding buffer, lysed with 0.5 ml of 5M NaOH, and the entire lysate was counted. Nonspecific binding of tracer (NSB), determined in wells containing 1 $\mu$M of [NleTyr$^{8,21}$,Tyr$^{34}$]rPTH-(1–34)NH$_2$, was ~1% of total counts added. Maximum specific binding (B$_0$) was calculated as the total radioactivity bound to cells in the absence of unlabeled PTH ligand, minus NSB. IC$_{50}$ values (the dose of competing ligand that resulted in 50% inhibition of $^{125}$I[NleTyr$^{8,21}$,Tyr$^{34}$]rPTH-(1–34)NH$_2$ binding) were determined from plots of log(B/B$_0$–B) vs. log[competitor]. For Scatchard analyses, homologous competition binding studies were performed that used $^{125}$I-[NleTyr$^{8,21}$,Tyr$^{34}$]rPTH-(1–34)NH$_2$ (26 fmole /well) and varying amounts (1.2–300 pmol) of the same unlabeled ligand. Estimates of the number of receptors/cell derived from these studies assumed a single class of binding sites and a transfection efficiency of 20% (Abou-Samra, A. B. et al., *Proc. Natl. Acad. Sci (USA)* 89:2732–2736 (1992)).

Intracellular Cyclic AMP

Transfected COS-7 cells were rinsed with 500 ml of binding buffer. 200 $\mu$l of IBMX buffer (DMEM containing 2 mM IBMX, 1 mg/ml bovine serum albumin, 35 mM Hepes-NaOH, pH 7.4) and 100 ml of binding buffer or binding buffer containing various amounts of a PTH or PTHrP analog were then added. The plates were incubated for 60 minutes at room temperature. The buffer was then withdrawn and the cells lysed by placing the plates on powdered dry ice and adding 0.5 ml of 50 mM HCl. The acid lysate was diluted 1/30 in dH$_2$O, and an aliquot (5–50 $\mu$l) analyzed for cAMP content by radioimmunoassay. EC$_{50}$ values (the dose of ligand that resulted in 50% of the maximum response (E$_{max}$) obtained for that ligand with the relevant receptor) were determined from plots of log(E/E$_{max}$–E) vs. log[ligand], where E is the cAMP response measured at the corresponding dose of ligand. For antagonist studies, the inhibitor peptide [Leu$^{11}$,D-Trp$^{12}$]hPTHrP (7–34)NH$_2$ or [Trp$^{23}$,Tyr$^{36}$]hPTHrP-(1–36)N$_2$H was applied to COS-7 cells in 100 $\mu$l of binding buffer two minutes prior to the addition of IBMX buffer that contained a near-maximal stimulatory dose (1.5 nM) of [Tyr$^{34}$]hPTH-(1–34) NH$_2$ agonist peptide. The cells were then incubated for 30 minutes at room temperature, and the resulting intracellular cAMP was measured by RIA. Data were analyzed using the AssayZap software (Elsevier Science Publishers BV, Cambridge, United Kingdom).

Results

The binding and cAMP-signaling responses obtained for PTH-(1–34) ([Tyr$^{34}$]hPTH-(1–34)NH$_2$) (SEQ ID NO:1) and PTHrP-(1–36) ([Tyr$^{36}$]hPTHrP-(1–36)NH$_2$) (SEQ ID NO:2) in COS-7 cells expressing the human PTH/PTHrP and human PTH-2 receptors are shown in FIG. 1. With the PTH/PTHrP receptor, both PTH-(1–34) and PTHrP-(1–36) fully inhibited binding of the radioligand, $^{125}$I-[NleTyr$^{8,21}$, Tyr$^{34}$]rPTH-(1–34)NH$_2$, although PTH-(L1–34) was 4.8-fold more potent than PTHrP-(1–36) (IC$_{50}$s=39 and 285 nM, respectively, p<0.001; FIG. 1A and Table 1). With cells expressing the PTH-2 receptor, PTH-(1–34) bound with high apparent affinity, while PTHrP-(1–36) bound poorly with a potency that was more than 100-fold weaker than that of PTH-(1–34) (FIG. 1B and Table 1).

Figure 1C:
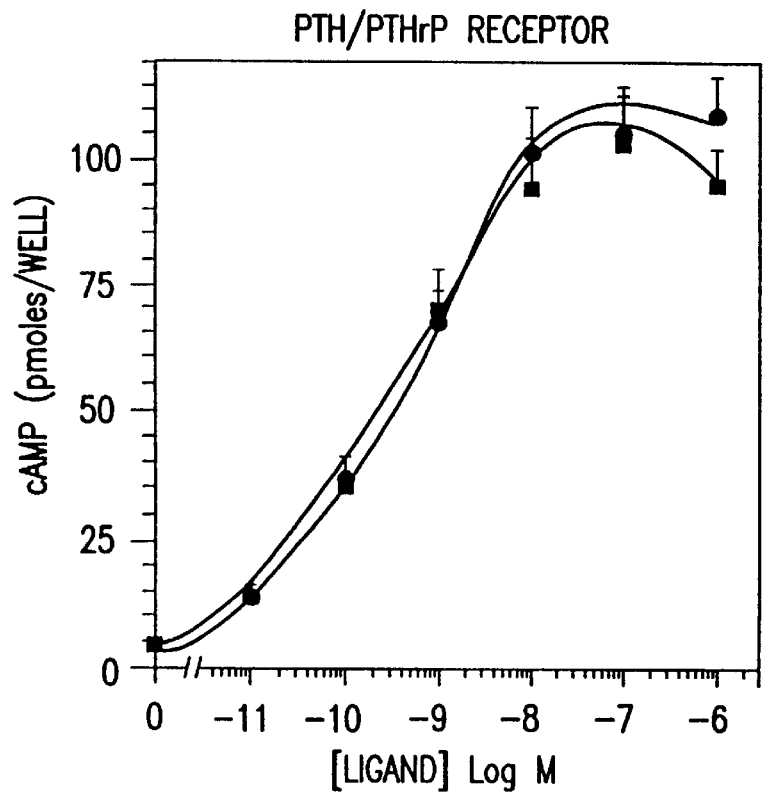
Figure 1D:
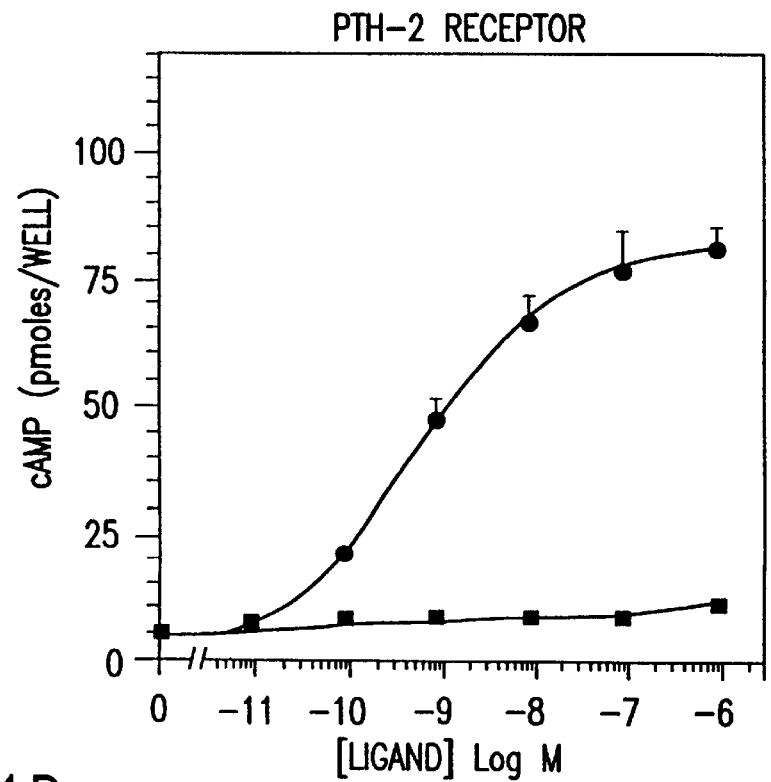

Both PTH-(1–34) and PTHrP-(1–36) were full and potent agonists of cAMP production in COS-7 cells expressing the PTH/PTHrP receptor (FIG. 1C and Table 2). In contrast, only PTH-(1–34) was a potent agonist with the PTH-2 receptor, while PTHrP-(1–36) was nearly inactive (FIG. 1D). These results confirm the markedly different cAMP-stimulating activities of PTH and PTHrP with the PTH-2 receptor (Usdin, T. et al., *J. Biol. Chem.* 270:15455–15458 (1995)), and demonstrate that at least part of the signaling defect that PTHrP has with this receptor can be attributed to weak binding interactions.

Scatchard analyses of competition binding data indicated that the PTH-2 receptor was expressed on the surface of COS-7 cells to levels that were 5-fold lower than the level of expression attained by the PTH/PTHrP receptor (FIGS. 2A and 2B). This difference in expression levels is likely to explain the lower cAMP responses compared to the PTH/PTHrP receptor (FIG. 1). Although, the reason for the lower expression of the PTH-2 receptor is unclear at present, expression was fully adequate for comparing the interactions of different PTH and PTHrP analogs with this receptor.

TABLE 2

Receptor-binding properties of PTH and PTHrP analogs
COS-7 cells transfected with plasmids encoding the human PTH/PTHrP receptor or the human PTH-2 receptor were stimulated with the indicated ligand for 1 h at room temperature, and the resulting levels of intracellular cAMP were quantified by RIA. The maximum values indicate the highest level of cAMP that was attained for each ligand with each receptor. The mean basal cAMP values (not subtracted) were 4.6 ± 0.2 and 5.4 ± 0.3 pmoles/well for the PTH/PTHrP and PTH-2 receptors, respectively. Data are the mean (±s.e.m.) of values obtained from the number of experiments indicated (n).

| | cAMP accumulation | | | | | |
|---|---|---|---|---|---|---|
| | PTH/PTHrP receptor | | | PTH-2 receptor | | |
| Ligand | EC50 (nM) | Maximum (pmoles/well) | (n) | EC50 (nM) | Maximum (pmoles/well) | (n) |
| [Y34]hPTH-(1–34)NH2 (SEQ ID NO: 1) | 0.46 ± 0.18 | 113 ± 13 | 5 | 0.6 ± 0.1 | 81 ± 5 | 5 |
| [Y36]hPTHrP-(1–36)NH2 (SEQ ID NO: 2) | 0.32 ± 0.04 | 103 ± 10 | 5 | >1000 | 11 ± 1 | 5 |
| [15, Y36]hPTHrP-(1–36)NH2 | 0.26 ± 0.08 | 112 ± 9 | 3 | 7.0 ± 2.1 | 80 ± 5 | 3 |
| [W23,Y36]hPTHrP-(1-36)NH2 | 0.26 ± 0.05 | 123 ± 14 | 4 | >1000 | 12 ± 1 | 4 |

TABLE 2-continued

Receptor-binding properties of PTH and PTHrP analogs
COS-7 cells transfected with plasmids encoding the human PTH/PTHrP receptor or the human PTH-2 receptor were stimulated with the indicated ligand for 1 h at room temperature, and the resulting levels of intracellular cAMP were quantified by RIA. The maximum values indicate the highest level of cAMP that was attained for each ligand with each receptor. The mean basal cAMP values (not subtracted) were 4.6 ± 0.2 and 5.4 ± 0.3 pmoles/well for the PTH/PTHrP and PTH-2 receptors, respectively. Data are the mean (±s.e.m.) of values obtained from the number of experiments indicated (n).

| | cAMP accumulation | | | | | |
|---|---|---|---|---|---|---|
| | PTH/PTHrP receptor | | | PTH-2 receptor | | |
| Ligand | EC50 (nM) | Maximum (pmoles/well) | (n) | EC50 (nM) | Maximum (pmoles/well) | (n) |
| [15, W23, Y36]hpTHrP-(1-36)NH2 | 0.21 ± 0.06 | 109 ± 10 | 4 | 0.5 ± 0.3 | 65 ± 7 | 4 |
| [H5,Y34]hPTH-(1-34)NH2 | 0.93 ± 0.37 | 116 ± 19 | 3 | >1000 | 10 ± 1 | 3 |
| [F23, Y34]hPTH-(1-34)NH2 | 0.23 ± 0.02 | 104 ± 16 | 4 | 7.6 ± 2.2 | 50 ± 8 | 4 |
| [H5, F23, Y34]hPTH-(1-34)NH2 | 1.18 ± 0.29 | 110 ± 19 | 3 | >1000 | 7.1 ± 0.9 | 3 |
| Hybrid-1 (SEQ ID NO: 3) [Y34]hPTHrP-(1–14)/hPTH-(15–34)NH2 | 0.23 ± 0.04 | 140 ± 17 | 3 | >1000 | 5.3 ± 0.6 | 3 |
| Hybrid-5 (SEQ ID NO: 4) [Y34]hPTHrP-(1–18)/hPTH-(19–34)NH2 | 0.43 ± 0.16 | 133 ± 14 | 3 | >1000 | 6.2 ± 0.4 | 3 |
| Hybrid-4 (SEQ ID NO: 5) [Y34]hPTHrP-(1–21)/hPTH-(22–34)NH2 Hybrid-3 (SEQ ID NO: 6) | 0.27 ± 0.06 | 107 ± 17 | 4 | >1000 | 6.7 ± 0.6 | 4 |

PTH/PTHrP Hybrid Ligands

To localize regions of PTH and PTHrP responsible for the difference in apparent binding affinities of the two ligands with the PTH-2 receptor, the inventors evaluated the series of PTH/PTHrP hybrid analogs shown in FIG. 3. (Seq ID NOS:3–7) Some of the hybrid ligands (i.e., hybrids 1 and 5) were not highly informative, because unlike either parent ligand, they competed poorly for binding even to the PTH/PTHrP receptor, indicating that these analogs were unlike either parent ligand. Similarly weak binding potencies for these hybrid ligands were previously observed in studies with rat osteosarcoma cells (ROS 17/2.8). Those results were interpreted as alterations in ligand structure caused by incompatibility between residues in the amino-terminal 1–14 portion of PTHrP and the 15–34 region of PTH (Gardella, T. J. et al., *J. Biol. Chem.* 270:6584–6588 (1995)). For the current studies on the PTH-2 receptor, the most informative hybrid analogs were hybrid-3 and hybrid-4. Hybrid-4 (SEQ ID NO:5), PTHrP-(1–21)/PTH-(22–34) bound to the PTH-2 receptor with high potency ($IC_{50}$=11 nM), similar to PTH-(1–34) (Table 1). Extending the PTHrP sequence by two residues yielded hybrid-3 (SEQ ID NO:6), PTHrP-(1–23)/PTH-(24–34), which competed poorly for binding to the PTH/PTHrP receptor ($IC_{50}$=1,000 nM), and bound with even weaker potency to the PTH-2 receptor (IC50~6,000 nM). In this regard, the binding profile of hybrid-3 resembled that of PTHrP-(1–36).

Substitutions at Positions 22 and 23

Figure 4A:
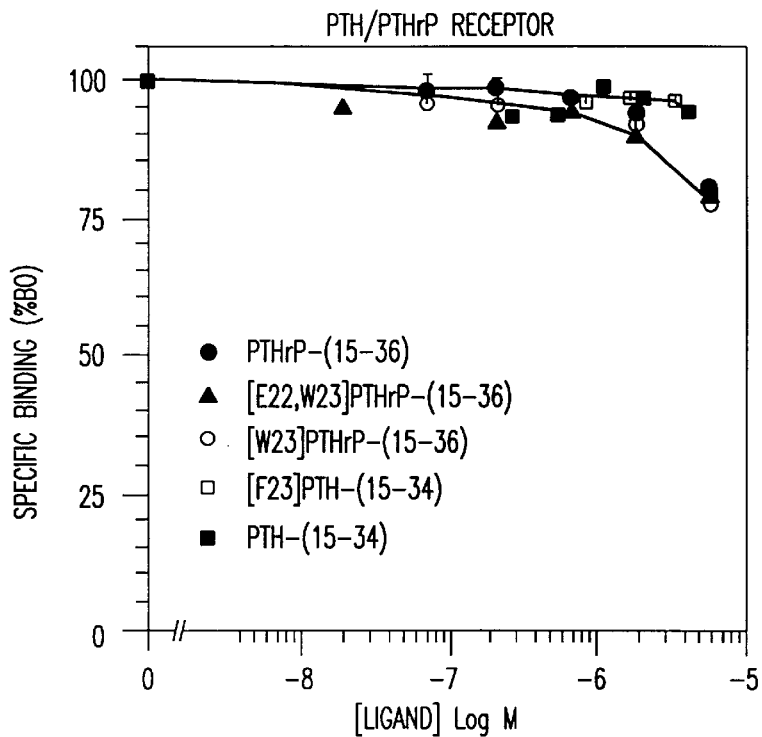
FIG. 4 depicts the effects of substitutions at position 23 on the binding properties of PTH-(15–34) and PTHrP-(15–36) carboxy-terminal fragments. The binding properties of substituted and unsubstituted PTH-(15–34) or PTHrP-(15–36) to COS-7 cells expressing either PTH/PTHrP receptors (FIG. 4A) or PTH-2 receptors (FIG. 4B) are shown. Competition-binding studies were performed at room temperature for 2 hours with $^{125}$I-[NleTyr$^{8,21}$,Tyr$^{34}$]rPTH-(1–34)NH$_2$ (100,000 CPM/well) as radioligand. The unlabeled competitor ligands used are indicated in the figure key, the structure of each was based on the human PTH or PTHrP sequence and contained tyrosine-amide as a carboxy-terminal residue. Data are the mean (±s.e.m.) of 3 or 4 experiments, each performed in duplicate.
Figure 4B:
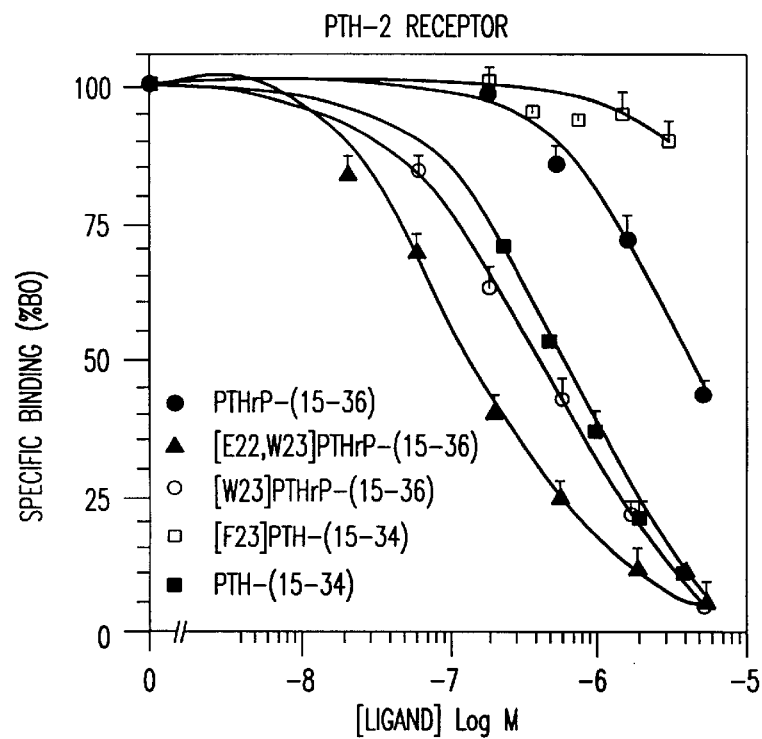

Comparing the structures and binding properties of hybrids 3 and 4 led the inventors to hypothesize that the divergent residues at positions 22 and/or 23 contribute to PTH-2 receptor binding selectivity. To initially test the role of residues 22 and 23 in receptor binding, shorter-length PTHrP-(15–36) fragments were prepared in which Phe-22 and/or Phe-23 were replaced by the corresponding Glu and Trp residues of PTH. The unsubstituted parent peptide, PTHrP-(15–36), competed weakly for binding to the PTH-2 receptor (FIG. 4B). The binding potency improved considerably with the combined Glu-22 and Trp-23 to Glu and Trp substitution. Most of this enhancement could be accounted for by the single substitution of Trp for Phe-23 (Table 1, FIG. 4B). Binding of either unsubstituted or substituted PTHrP-(15–36) fragments to the PTH/PTHrP receptor could not be detected within these competition assays (FIG. 4A).

Figure 5A:
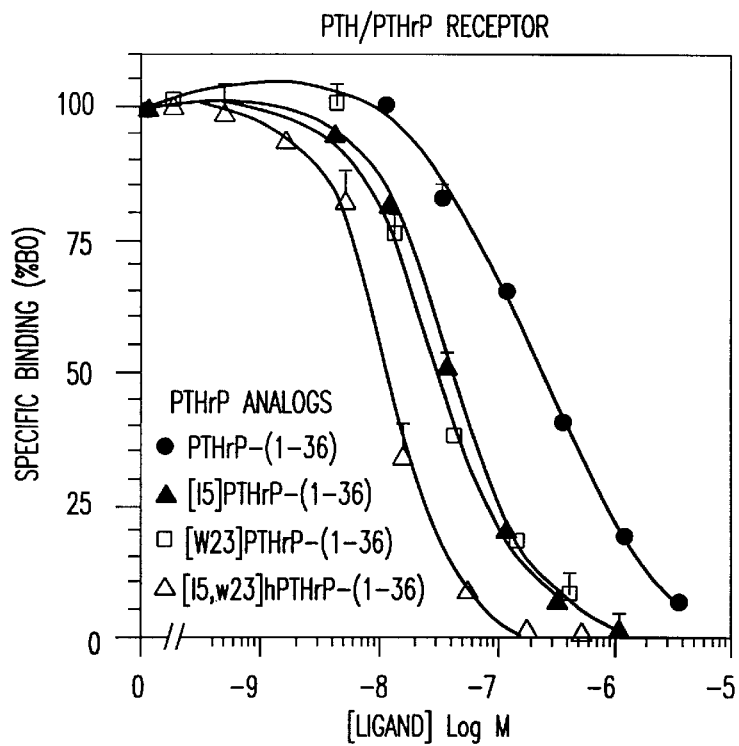
FIG. 5 depicts the effects of substitutions at position 5 and 23 on the binding of PTH-(1–34) and PTHrP-(1–36) to PTH/PTHrP and PTH-2 receptors. The binding of substituted or unsubstituted PTH-(1–34) or PTHrP-(1–36) analogs to COS-7 cells expressing either PTH/PTHrP receptors (FIGS. 5A and 5C) or PTH-2 receptors (FIGS. 5B and 5D) are shown. Competition-binding studies (RT/2h) were performed with $^{125}$I-[NleTyr$^{8,21}$,Tyr$^{34}$]rPTH-(1–34)amide (100,000 CPM/well) as radioligand. The unlabeled PTHrP (FIGS. 5A and 5B) and PTH (FIGS. 5C and 5D) analog ligands, used as competitors, are indicated in the figure keys; the structure of each was based on the human PTH or PTHrP sequence and contained tyrosine-amide as a carboxy-terminal residue. The binding curves of [Tyr$^{36}$]hPTHrP-(1–36)NH$_2$, and [Tyr$^{34}$]hPTH-(1–34)NH$_2$ from FIGS. 1A and B are shown again for comparison. Data are the mean (±s.e.m.) of 3–10 experiments, each performed in duplicate.
Figure 5B:
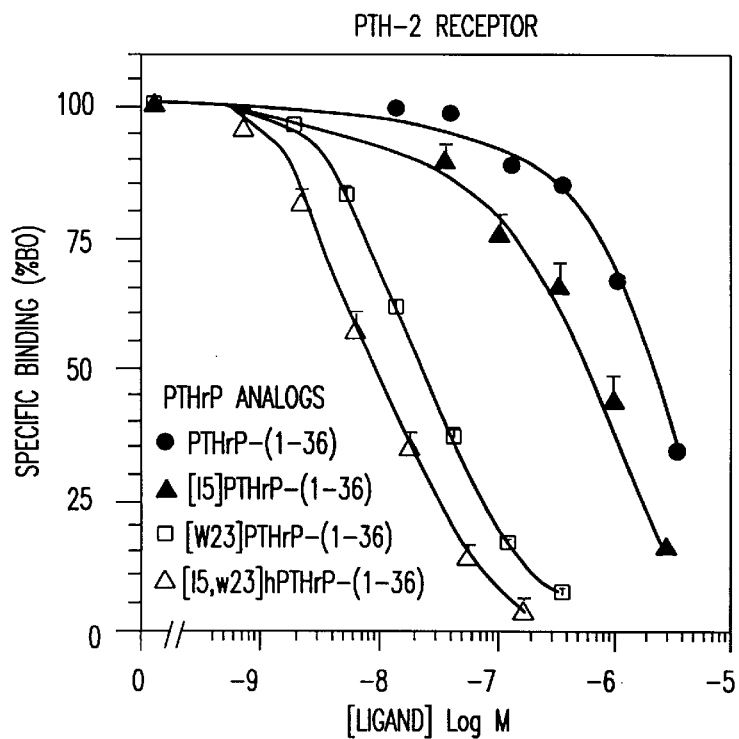
Figure 5C:
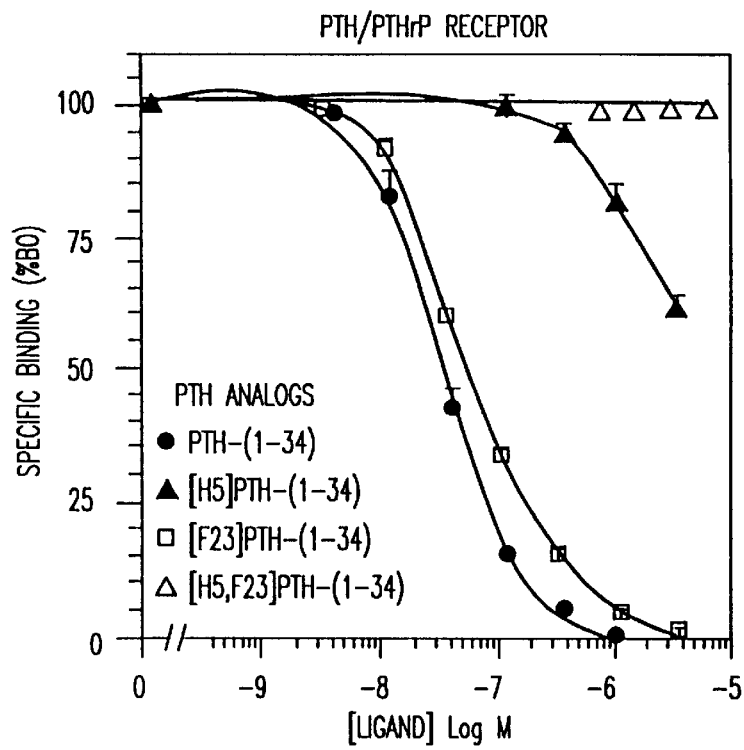
Figure 5D:
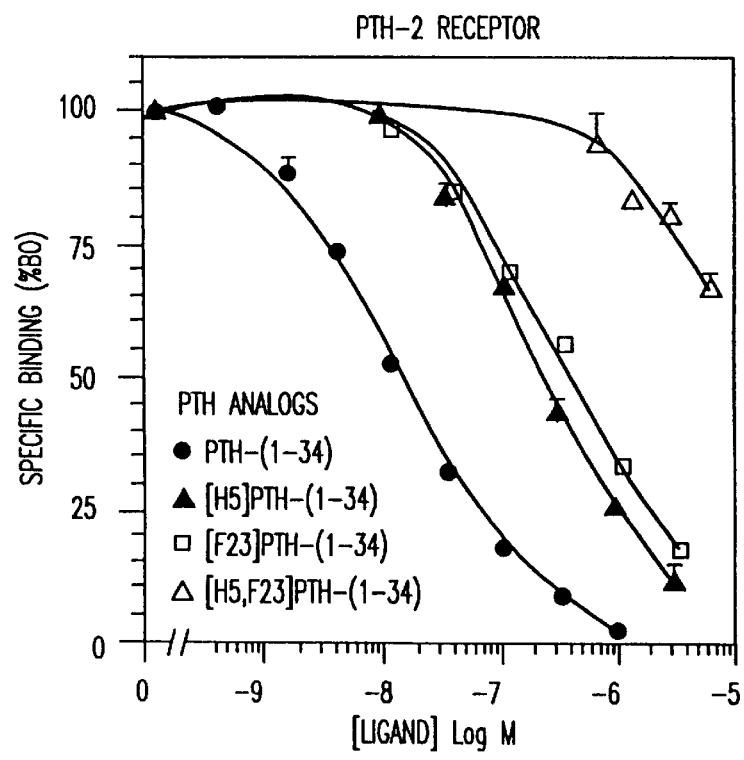

The Phe-23-to-Trp modification was introduced into full-length PTHrP-(1–36), where it was found to enhance binding potency for the PTH-2 receptor by 71-fold, as compared to the binding of PTHrP-(1–36) itself (FIG. 5B; Table 1). The reciprocal change of Trp-23-to-Phe in PTH-(1–34) led to a 28-fold reduction in binding potency for the PTH-2 receptor, as compared to unsubstituted PTH-(1–34) (FIG. 5D and Table 1). Interestingly, the divergent residues at position 23 could also account for some of the difference in the apparent binding affinities that PTH and PTHrP exhibited for the PTH/PTHrP receptor. Thus, [$Trp^{23}$]PTHrP-(1–36) bound to the PTH/PTHrP receptor with 6-fold stronger affinity than did PTHrP-(1–36) (FIG. 5A; Table 1), and [$Phe^{23}$]PTH-(1–34) bound to this receptor with 2–3 fold weaker affinity than did PTH-(1–34) (FIG. 5C; Table 1). The effect of these position 23 changes on binding to the PTH/PTHrP receptor could be predicted from the binding properties that hybrid-3 and hybrid-4 displayed with this receptor (Table 1).

Effects of Residues 5 and 23 on cAMP Signaling

Figure 6A:
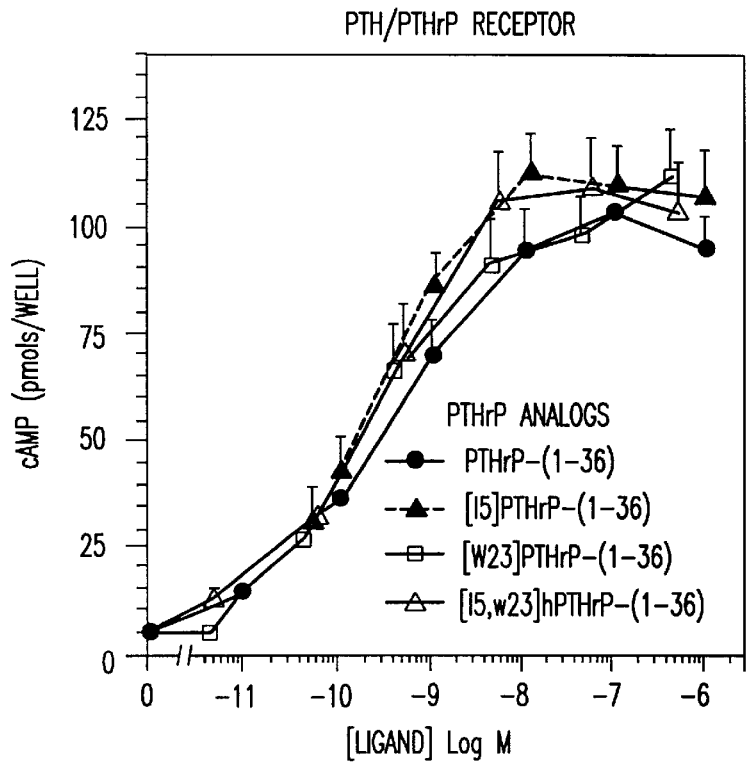
FIG. 6 depicts the effects of substitutions at positions 5 and 23 on cAMP signaling by PTH-(1–34) and PTHrP-(1–36) with PTH/PTHrP and PTH-2 receptors. The abilities of substituted and unsubstituted PTH-(1–34) or PTHrP-(1–36) peptide analogs to stimulate cAMP formation in COS-7 cells expressing either PTH/PTHrP receptors (FIGS. 6A and 6C) or PTH-2 receptors (FIGS. 6B and 6D) are shown. Cells were treated with the indicated amount of peptide for 1 hour at room temperature in the presence of IBMX. The PTHrP (FIGS. 6A and 6B) and PTH (FIGS. 6C and 6D) analog ligands used are indicated in the figure keys; each was based on the human PTH or PTHrP sequence and contained tyrosine-amide as a carboxy-terminal residue. The curves of [Tyr$^{36}$]hPTHrP-(1–36)NH$_2$, and [Tyr$^{34}$]hPTH-(1–34)NH$_2$ from FIGS. 1C and 1D are shown again here for comparison. Data are the mean (±s.e.m.) of 3–5 experiments, each performed in duplicate.
Figure 6B:
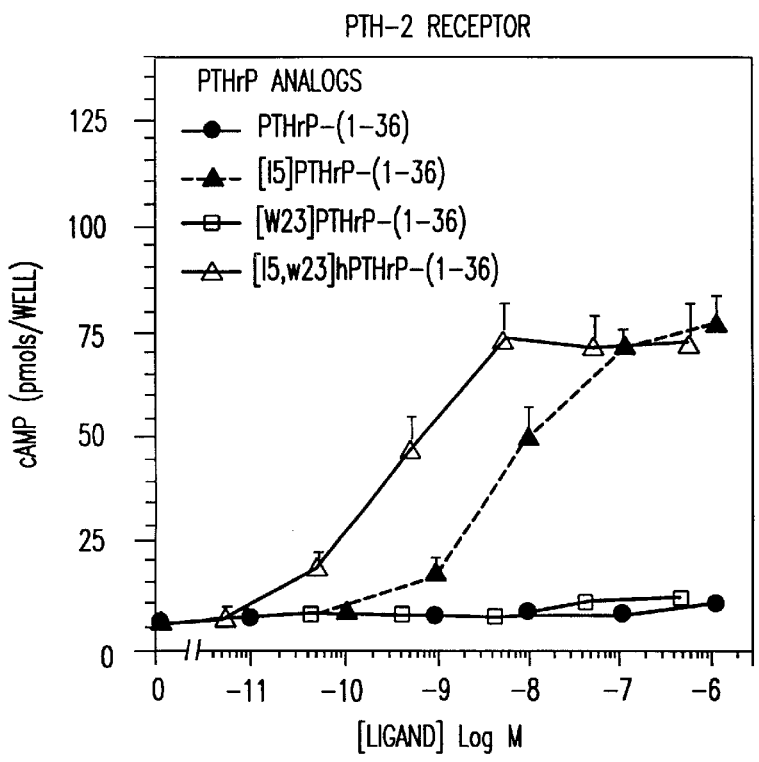
Figure 6C:
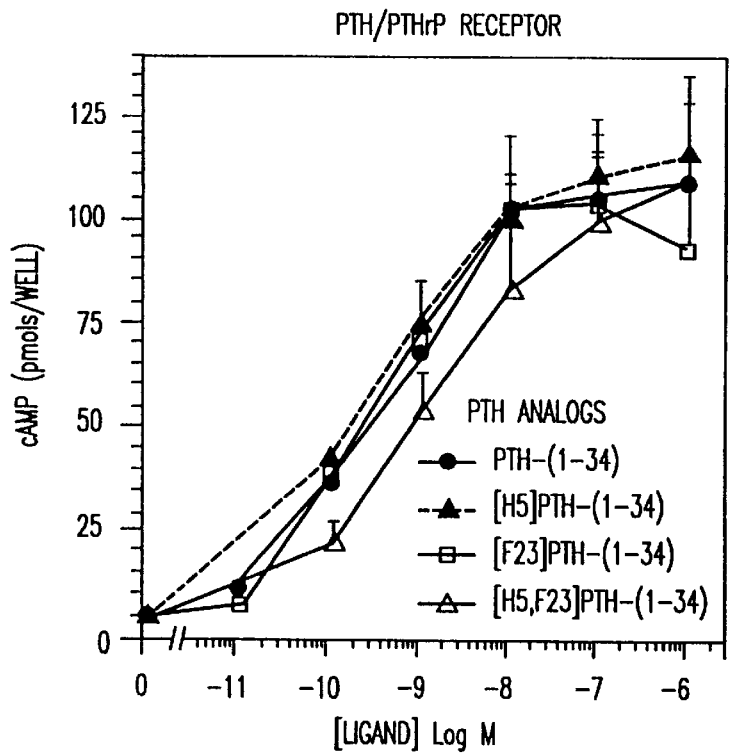
Figure 6D:
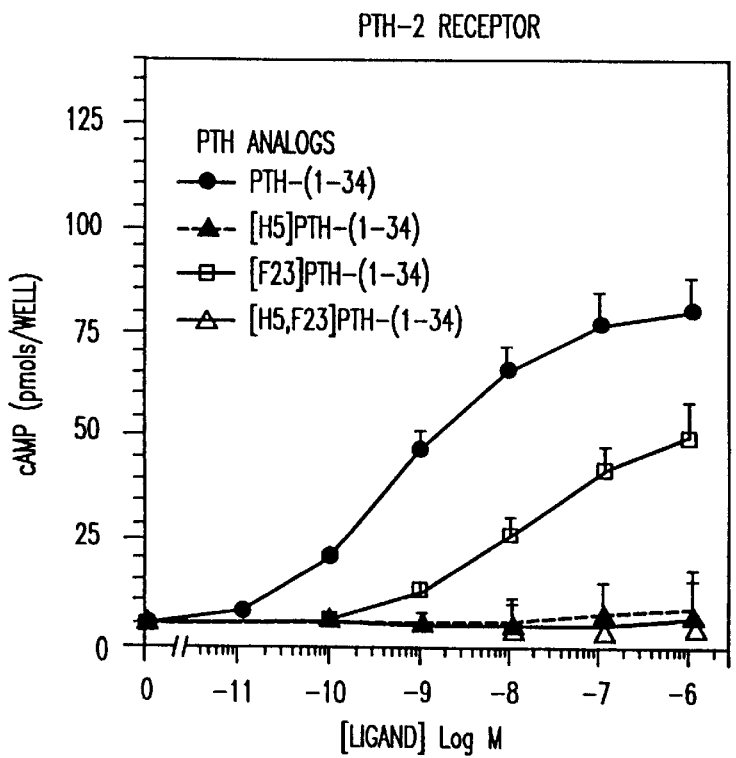

The above substitutions at position 23 in PTH or PTHrP had little or no effect on cAMP-signaling by the PTH-2 receptor; [$Trp^{23}$]PTHrP-(1–36) was still inactive and [$Phe^{23}$]PTH-(1–34) was nearly a full agonist (FIGS. 6B and 6D; Table 2). The high potency of hybrid-2 (SEQ ID NO:7), PTH-(1–14)/PTHrP-(15–34), in stimulating cAMP production with the PTH-2 receptor, compared with the weak activity of hybrid-1 (SEQ ID NO:3), PTHrP-(1–14)/PTH-(15–34) (Table 2), suggested that residues within the 1–14 sequence of PTH and PTHrP were involved in modulating the signaling properties of the two ligands with this receptor.

Previous binding studies in ROS 17/2.8 cells revealed that position 5 (Ile in PTH and His in PTHrP) was one divergent site in the 1–14 region that could dramatically affect ligand-receptor interaction (Gardella, T. J. et al., *J. Biol. Chem.* 270:6584–6588 (1995)). Therefore, the effects of reciprocal position 5 substitutions on signaling interactions with the PTH-2 receptor were tested. Strikingly, [$Ile^5$]PTHrP-(1–36) became a full agonist with the PTH-2 receptor, promoting the same maximal cAMP response as that attained by PTH-(1–34) (FIG. 6B and Table 2). However, the $EC_{50}$ of the [Ile$^5$]PTHrP-(1–36) response was still 12-fold higher than that of PTH-(1–34) ($EC_{50}$s=7 and 0.6 nM, respectively). The inventors, therefore, combined the Ile-5 substitution with the affinity-enhancing Trp-23 modification. The resulting analog, [Ile$^5$,Trp$^{23}$]PTHrP-(1–36), was as potent and efficacious as PTH-(1–34) in both binding and cAMP production with the PTH-2 receptor (FIG. 6B, Tables 1 and 2).

Figure 7A:
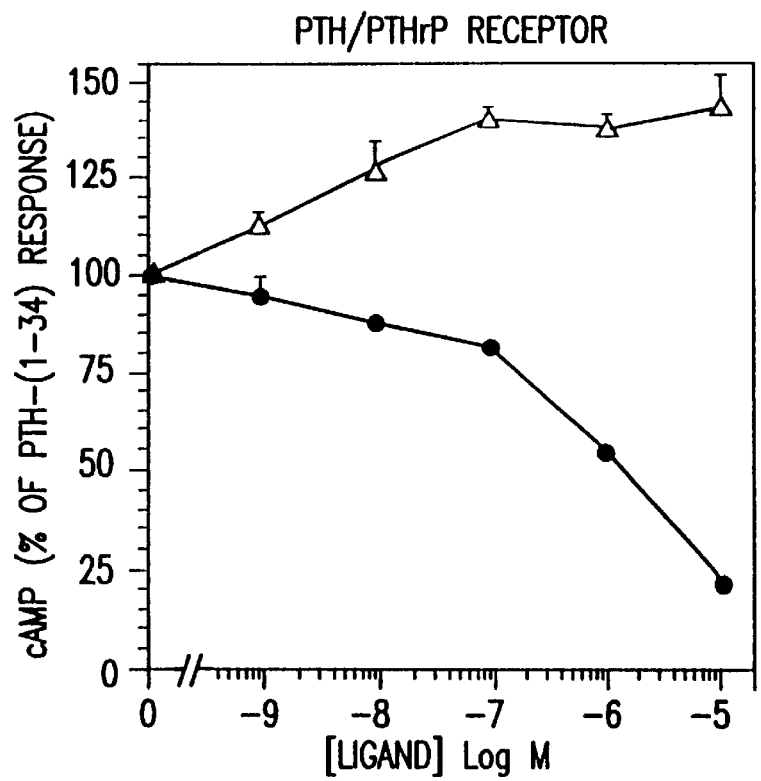
FIG. 7 depicts the antagonism of PTH-(1–34)-induced cAMP formation in COS-7 cells expressing PTH/PTHrP or PTH-2 receptors. COS-7 cells expressing either PTH/PTHrP or PTH-2 receptors were treated with varying doses of [Leu$^{11}$,D-Trp$^{12}$]hPTHrP(7–34)NH$_2$ or [Trp$^{23}$,Tyr$^{36}$]hPTHrP-(1–36), plus a near-maximal stimulatory dose of the agonist, [Tyr$^{34}$]hPTH-(1–34)NH$_2$ (1 nM), and then incubated in the presence of IBMX for 30 minutes at room temperature. The resulting intracellular cAMP levels are expressed as the percent of the cAMP levels in cells treated with [Tyr$^{34}$]hPTH-(1–34)NH$_2$ alone (1 nM), which were 167±17 and 70±8 pmoles/well for the PTH/PTHrP receptor and the PTH-2 receptor, respectively. The corresponding basal cAMP levels in cells not treated with peptide were 8.4±0.3 and 9.0±11.7 pmoles/well, respectively. Data are the mean (±s.e.m.) of two experiments, each performed in duplicate.
Figure 7B:
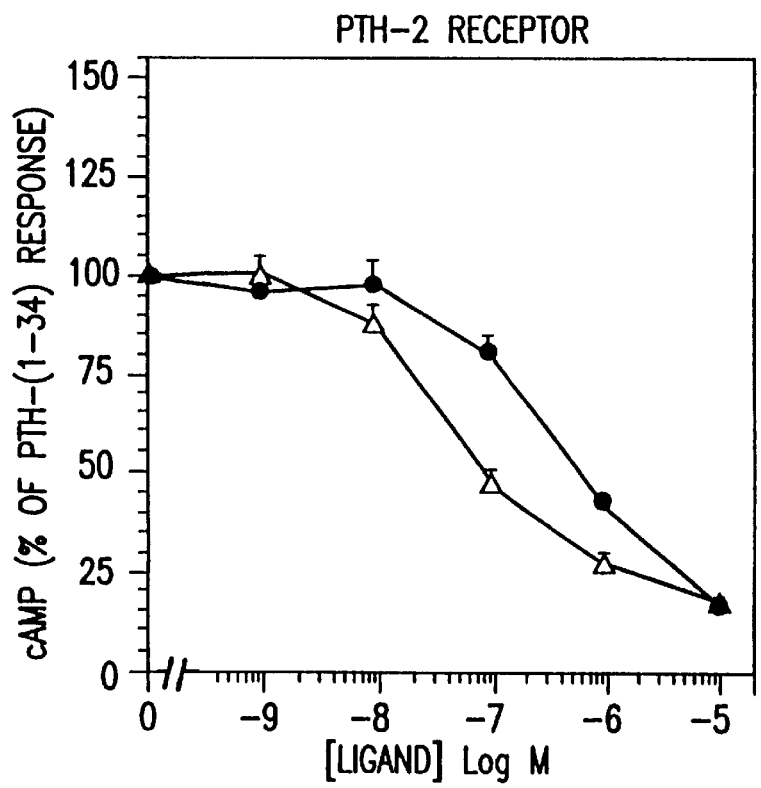

The observation that [Trp$^{23}$]PTHrP-(1–36) (histidine at position 5) bound to the PTH-2 receptor without stimulating cAMP production, suggests that this analog could function as a PTH-2 receptor antagonist. FIG. 7 shows that this analog was indeed at least as potent as [Leu$^{11}$,D-Trp$^{12}$] hPTHrP(7–34)NH$_2$, a highly potent antagonists of the PTH/PTHrP receptor antagonist (Nutt et al., *Endocrinology* 127:491–493 (1990)), in inhibiting PTH-(L1–34)-induced activity on the PTH-2 receptor. With the PTH/PTHrP receptor, [Trp$^{23}$]PTHrP-(1–36) was not an antagonist, but instead augmented the agonist response to PTH-(1–34).

Discussion

The studies discussed above demonstrate that the failure of PTHrP to efficiently bind to and activate the PTH-2 receptor can be attributed to two residues, phenylalanine at position 23 and histidine at position 5. In PTH, which is fully potent with the PTH-2 receptor, these residues are replaced by tryptophan and isoleucine, respectively. By exchanging residues 5 and 23 of PTHrP with the corresponding isoleucine and tryptophan residues of PTH, PTHrP could be converted into a full and potent PTH-2 receptor agonist.

The histidine at position-5 in PTHrP blocked activation of the PTH-2 receptor. In previous competition binding studies in ROS 17/2.8 cells, residue 5 was identified as an important determinant for interacting with the PTH/PTHrP receptor (Gardella, T. J. et al., *J. Biol. Chem.* 270:6584–6588 (1995)). These earlier studies suggested that this residue was involved in putative intramolecular interactions between the 1–14 and with the 15–34 portions of the ligand. Evidence for this included the ability of the His-5-to-Ile-5 substitution in PTHrP to "cure" the deleterious effects that carboxy-terminal substitutions (i.e. at positions, 19, 21 and 24) had on binding potency. It now appears that the full role of residue 5 in the ligand in PTH and PTHrP is more complex, since the present data indicate that this residue strongly modulates signaling interactions with the PTH-2 receptor.

The weak binding of PTHrP to the PTH-2 receptor can be attributed to the phenylalanine residue at position 23; replacing this residue by the corresponding tryptophan of PTH improved binding to the PTH-2 receptor by 71-fold. The substitution of Trp for Phe-23 could also explain the six-fold weaker binding that PTHrP-(1–36) exhibited for the PTH/PTHrP receptor, as compared to PTH-(1–34) (Table 1). Such weaker binding of PTHrP was observed in earlier studies with the cloned human PTH/PTHrP receptor expressed in COS-7 cells, although, nearly equivalent binding potencies were seen with the cloned rat PTH/PTHrP receptor (Schipani, E. et al., *Endocrinology* 132:2157–2165 (1993)). Earlier studies with the rat PTH/PTHrP receptor endogenous to ROS 17/2.8 cells also found comparable binding potencies for the two ligands (Jüppner, H. et al., *J. Biol. Chem.* 263:8557–8560 (1988); Nissenson, R. A. et al., *J. Biol Chem.* 263:12866–12871 (1988)). Therefore, it may be expected that the rat and human PTH/PTHrP receptors, and the human PTH-2 receptor, each differ at a site or sites that recognize residue 23 in the ligand. Thus, with both receptors, the tryptophan-23 Trp modification in PTHrP enhanced the binding affinity of the analog to nearly that of PTH-(1–34).

The effects on activity of a variety of modifications at position 23 in PTH have been investigated previously in PTH/PTHrP receptors. Rosenblatt and coworkers found that the addition of a bulky ortho-nitrophenylsulfenyl group to the indole nitrogen of Trp-23 had little or no effect on bioactivity (Rosenblatt, M. & Potts, J. T., *Endo. Res. Comm.* 4:115–133 (1977)), nor did a napthylalanine substitution at this site (Nakamoto, C. et al., *Biochemistry* 34:10546–10552 (1995)). However, methylation of the backbone nitrogen at Phe-23, or, the substitution of D-Trp for Trp-23, severely reduced receptor-binding affinity (Caulfield, M. P. & Rosenblatt, M., *T.E.M.* Jan/Feb:164–168 (1990)). Mutational analysis of residues 23–34 of PTH-(1–84) showed that cysteine substitution of Trp-23 reduced bioactivity by more than 10-fold, while leucine substitution reduced activity by 50% (Gardella, T. J. et al., "Scanning mutagenesis of the 23–25 region of parathyroid hormone reveals important determinants of receptor binding," in *Calcium Regulating Hormones and Bone Metabolism; Basic and Clinical Aspects*, Vol. 11, Cohn, D. V. et al., eds., Elsevier Science Publishers BV, Amsterdam (1992), pp. 218–222). NMR studies on PTH analogs (Barden, J. A. & Kemp, B. E., *Biochemistry* 32:7126–7132 (1993); Marx, U. et al., *J. Biol. Chem.* 270:15194–15202 (1995); Klaus, W. et al., *Biochemistry* 30:6936–6942 (1991); Bundi, A. et al., *Eur. J. Biochem.* 91:201–208 (1978)) and PTHrP analogs (Barden, J. A. & Kemp, B. E., *Eur. J. Biochem.* 184:379–394 (1989); Ray, F. R. et al., *Eur. J. Biochem.* 211:205–211 (1993)) suggest that the aromatic residue at this position in either ligand is involved in intramolecular hydrophobic interactions. Residue 23 may, therefore, be important for maintaining ligand structure, as well as modulating receptor-binding interactions.

Because the PTHrP-(1–36) analog containing the Trp-23 modification exhibited high binding affinity for the PTH-2 receptor without having detectable agonist activity, we evaluated it as a potential PTH-2 receptor antagonist. This analog was at least as potent as [Leu$^{11}$,D-Trp$^{12}$]hPTHrP (7–34)NH$_2$ a previously characterized antagonist of the PTH/PTHrP receptor in inhibiting the agonist action of PTH-(1–34) on the PTH-2 receptor; however, unlike the amino-terminally truncated antagonist analog, however, [Trp$^{23}$]PTHrP-(1–36) was a full and potent agonist with the PTH/PTHrP receptor (FIGS. 6A and 7A). Because this new analog appears to be a selective antagonist for the PTH-2 receptor, it could potentially be useful to in vivo studies aimed at further elucidating the physiological role of the PTH-2 receptor.

PTHrP is expressed in many fetal and adult tissues and is a vital developmental morphogen, a function that is likely to be mediated by the PTH/PTHrP receptor (Karaplis, A. C. et al., *Genes & Dev.* 8:277–289 (1994)). It is of interest that phenylalanine is preserved at position 23 in all native PTHrP ligands, despite the implications of the invention that tryptophan at this site, as is found in all native PTH ligands, is fully compatible with binding to the PTH/PTHrP receptor. It may be that phenylalanine has been selected for at position 23 in PTHrP, because of its ability to inhibit binding to the PTH-2 receptor. Likewise, the conserved histidine residue at position 5 in PTHrP may have been selected for because it blocks signaling interactions with the PTH-2 receptor. Together, these two conserved residues in PTHrP would thus ensure that productive interactions with the PTH-2 receptor do not occur.

In summary, the present inventors have identified two sites in PTH and PTHrP that account for the ligand selectivity of the PTH-2 receptor. The inventors are now constructing chimeras between the PTH-2 and PTH/PTHrP receptors, as one approach towards identifying the cognate receptor sites involved in this ligand selectivities for the two ligands. The functional profiles of such receptor chimeras interacting with modified PTH and PTHrP ligands should help to refine and constrain models of the complexes formed between these peptide ligands and their G protein-coupled receptors.

Therapeutic Use

In accordance with yet a further aspect of the invention, there is provided a method for treating a medical disorder that results from altered or excessive action of the PTH-2 receptor, comprising administering to a patient a therapeutically efficient amount of a PTHrP analog, sufficient to inhibit activation of the PTH-2 receptor of said patient. In a preferred embodiment, the PTHrP analog used in the method has a single amino acid substitution of phenylalanine for tryptophan at position 23 of PTHrP. In a particular embodiment, the PTHrP analog is [Trp$^{23}$]PTHrP-(1–36).

In this embodiment, a patient who is suspected of having a disorder resulting from altered action of the PTH-2 receptor may be treated using the peptide analogs of the invention shown to be a selective antagonist of the PTH-2 receptor. Such antagonists include the compounds of the invention which have been determined (by the assays described herein) to interfere with PTH-2 receptor-mediated cell activation or other analogs having similar properties.

To administer the antagonist, the appropriate peptide is used in the manufacture of a medicament, generally by being formulated in an appropriate carrier or excipient such as, e.g., physiological saline, and administered intravenously, intramuscularly, subcutaneously, or orally, at a dosage that provides adequate inhibition of PTH binding to the PTH-2 receptor. Typical dosage would be 1 ng to 10 mg of the antibody or peptide per kg body weight per day.

In accordance with yet a further aspect of the invention, there is provided a method for treating osteoporosis, comprising administering to a patient a therapeutically efficient amount of a PTHrP analog, sufficient to activate the PTH/PTHrP receptor and the PTH-2 receptor of said patient. In a preferred embodiment, the PTHrP analog used in the method has an amino acid substitution of histidine for isoleucine at position 5 of PTHrP, as well as phenylalanine for tryptophan at position 23 of PTHrP. In a particular embodiment, the PTHrP analog is [Ile$^5$, Trp$^{23}$]PTHrP-(1–36). Similar dosages and administration as described above for the PTHrP antagonist, may be used for administration of a PTHrP agonist, e.g., for treatment of conditions such as osteoporosis.

By "agonist" is intended a ligand capable of enhancing or potentiating a cellular response mediated by the PTH-2 receptor. By "antagonist" is intended a ligand capable of inhibiting a cellular response mediated by the PTH-2 receptor. Whether any candidate "agonist" or "antagonist" of the present invention can enhance or inhibit such a cellular response can be determined using art-known protein ligand/receptor cellular response or binding assays, including those described elsewhere in this application.

It will be appreciated to those skilled in the art that the invention can be performed within a wide range of equivalent parameters of composition, concentration, modes of administration, and conditions without departing from the spirit or scope of the invention or any embodiment thereof.

What is claimed is:

1. A PTHrP of SEQ ID NO:2 that is a PTH-2 receptor agonist, as well as a PTH/PTHrP receptor agonist, wherein the amino acid sequence is altered at amino acid residues 5 and 23.

2. The PTHrP of claim 1, wherein said alteration at PTHrP amino acid residue 5 is an amino acid substitution of histidine for isoleucine, and said alteration at PTHrP amino acid residue 23 is an amino acid substitution of phenylalanine for tryptophan.

3. The PTHrP of SEQ ID NO:2 with the following modifications: $(Ile^5, Trp^{23})$PTHrP-(1–36).

4. A PTHrP of SEQ ID NO:2 that is a PTH-2 receptor selective antagonist, as well as a PTH/PTHrP receptor agonist, wherein the amino acid sequence is altered at amino acid residue 23.

5. The PTHrP of claim 4, wherein said alteration at PTHrP amino acid residue 23 is an amino acid substitution of phenylalanine for tryptophan.

6. The PTHrP of SEQ ID NO:2 with the following modification: $(Trp^{23})$PTHrP-(1–36).

* * * * *

UNITED STATES PATENT AND TRADEMARK OFFICE
CERTIFICATE OF CORRECTION

PATENT NO. : 6,147,186
DATED : November 14, 2000
INVENTOR(S) : Gardella and Jüppner It is certified that error appears in the above-identified patent and that said Letters Patent is hereby corrected as shown below:

Column 4,
Line 49, please delete "The insets" and insert therefore -- Figues 2A1 and 2B1 --.

Please delete Table 1

TABLE 1

Receptor-binding properties of PTH and PTHrP analogs COS-7 cells transfected with plasmids encoding the human PTH/PTHrP receptor or the human PTH-2 receptor were evaluated in competition binding studies that used [Nle$^{8,21}$, Y$^{34}$]rPTH-(1-34)NH$_2$ as radioligand and the indicated unlabeled ligands as competitors. Assays were performed for 2 hours at room temperature. Data are the means (s.e.m.) of IC$_{50}$ values obtained from the number of experiments indicated (n).

| Ligand | Binding IC50 (nM) | | | |
|---|---|---|---|---|
| | PTH/PTHrP receptor | (n) | PTH-2 receptor | (n) |
| [Nle8, 21, Y34]rPTH-(1-34)NH2 (SEQ ID NO: 1) | 58 ± 4 | 5 | 11 ± 2 | 5 |
| [Y34]hPTH-(1-34)NH2 | 39 ± 4 | 7 | 16 ± 4 | 7 |
| [Y36]hPTHrP-(1-36)NH2 (SEQ ID NO: 2) | 285 ± 47 | 10 | 2,140 ± 250 | 10 |
| Hybrid-1 (SEQ ID NO: 3) hPTHrP-(1-14)[Y34]hPTH-(15-34)NH2 | 7,900 ± 370 | 4 | 606 ± 96 | 4 |

| Ligand | cAMP accumulation | | | |
|---|---|---|---|---|
| | PTH/PTHrP receptor | | PTH-2 receptor | |
| | EC50 (nM) | Maximum (pmoles/well) | EC50 (nM) | Maximum (pmoles/well) |
| [Y34]hPTHrP-(1-23)hPTH-(24-34)NH2 | 0.42 ± 0.13 | 95 ± 9 | 4 | >1000 | 11 ± 3 | 4 |
| Hybrid-1 (SEQ ID NO: 7) [Y34]hPTH-(1-14)hPTHrP-(15-34)NH2 | 0.74 ± 0.37 | 123 ± 28 | 3 | 2.3 ± 0.5 | 58 ± 12 | 3 | and replace it with Table 1 on page 2 of 4.

In replacement Table 1, please remove "(SEQ ID NO: 1)" after "[Nle8, 21, Y34]rPTH-(1-34)NH2" and insert it after "[Y34]hPTH-(1-34)NH2".

UNITED STATES PATENT AND TRADEMARK OFFICE
CERTIFICATE OF CORRECTION

PATENT NO. : 6,147,186
DATED : November 14, 2000
INVENTOR(S) : Gardella and Jüppner It is certified that error appears in the above-identified patent and that said Letters Patent is hereby corrected as shown below:

Replaces Table 1.

TABLE 1

Receptor-binding properties of PTH and PTHrP analogs
COS-7 cells transfected with plasmids encoding the human PTH/PTHrP receptor or the human PTH-2 receptor were evaluated in competition binding studies that used [$Nle^{8,21}$, $Y^{34}$]rPTH-(1–34)$NH_2$ as radioligand and the indicated unlabeled ligands as competitors. Assays were performed for 2 hours at room temperature. Data are the mean (±s.e.m.) of $IC_{50}$ values obtained from the number of experiments indicated (n).

| Ligand | Binding IC50 (nM) | | | |
|---|---|---|---|---|
| | PTH/PTHrP receptor | (n) | PTH-2 receptor | (n) |
| [Nle8, 21, Y34]rPTH-(1–34)NH2 (SEQ ID NO: 1) | 58 ± 4 | 5 | 11 ± 2 | 5 |
| [Y34]hPTH-(1–34)NH2 | 39 ± 4 | 7 | 16 ± 4 | 7 |
| [Y36]hPTHrP-(1–36)NH2 (SEQ ID NO: 2) | 285 ± 47 | 10 | 2,140 ± 250 | 10 |
| Hybrid-1 (SEQ ID NO: 3) hPTHrP-(1–14)/[Y34]hPTH-(15–34)NH2 | 7,900 ± 370 | 4 | 606 ± 96 | 4 |

UNITED STATES PATENT AND TRADEMARK OFFICE
CERTIFICATE OF CORRECTION

PATENT NO. : 6,147,186
DATED : November 14, 2000
INVENTOR(S) : Gardella and Jüppner It is certified that error appears in the above-identified patent and that said Letters Patent is hereby corrected as shown below:

Please delete Table 2-continued

TABLE 2-continued

Receptor-binding properties of PTH and PTHrP analogs
COS-7 cells transfected with plasmids encoding the human PTH/PTHrP receptor or the human PTH-2 receptor were stimulated with the indicated ligand for 1 h at room temperature, and the resulting levels of intracellular cAMP were quantified by RIA. The maximum values indicate the highest level of cAMP that was attained for each ligand with each receptor. The mean basal cAMP values (not subtracted) were $4.6 \pm 0.2$ and $5.4 \pm 0.3$ pmoles/well for the PTH/PTHrP and PTH-2 receptors, respectively. Data are the mean ($\pm$ s.e.m.) of values obtained from the number of experiments indicated (n).

| | cAMP accumulation | | | | | |
|---|---|---|---|---|---|---|
| | PTH/PTHrP receptor | | | PTH-2 receptor | | |
| Ligand | EC50 (nM) | Maximum (pmoles/well) | (n) | EC50 (nM) | Maximum (pmoles/well) | (n) |
| [I5, W23, Y36]hPTHrP-(1-36)NH2 | $0.21 \pm 0.06$ | $109 \pm 10$ | 4 | $0.5 \pm 0.3$ | $65 \pm 7$ | 4 |
| [H5,Y34]hPTH-(1-34)NH2 | $0.93 \pm 0.37$ | $116 \pm 19$ | 3 | >1000 | $10 \pm 1$ | 3 |
| [F23, Y34]hPTH-(1-34)NH2 | $0.23 \pm 0.02$ | $104 \pm 16$ | 4 | $7.6 \pm 2.2$ | $50 \pm 8$ | 4 |
| [H5, F23, Y34]hPTH-(1-34)NH2 | $1.18 \pm 0.29$ | $110 \pm 19$ | 3 | >1000 | $7.1 \pm 0.9$ | 3 |
| Hybrid-1 (SEQ ID NO: 3) [Y34]hPTHrP-(1-14)/hPTH-(15-34)NH2 | $0.23 \pm 0.04$ | $140 \pm 17$ | 3 | >1000 | $5.3 \pm 0.6$ | 3 |
| Hybrid-5 (SEQ ID NO: 4) [Y34]hPTHrP-(1-18)/hPTH-(19-34)NH2 | $0.43 \pm 0.16$ | $133 \pm 14$ | 3 | >1000 | $6.2 \pm 0.4$ | 3 |
| Hybrid-4 (SEQ ID NO: 5) [Y34]hPTHrP-(1-21)/hPTH-(22-34)NH2 | $0.27 \pm 0.06$ | $107 \pm 17$ | 4 | >1000 | $6.7 \pm 0.6$ | 4 |
| Hybrid-3 (SEQ ID NO: 6) | | | | | | | and replace it with Table 2-continued on page 4 of 4.

In replacement Table 2-continued, please delete "Hybrid-1 (SEQ ID NO:7)" and insert therefor -- Hybrid-2 (SEQ ID NO: 7) --.

UNITED STATES PATENT AND TRADEMARK OFFICE
CERTIFICATE OF CORRECTION

PATENT NO. : 6,147,186
DATED : November 14, 2000
INVENTOR(S) : Gardella and Jüppner It is certified that error appears in the above-identified patent and that said Letters Patent is hereby corrected as shown below:

Replaces Table 2-continued.

TABLE 2-continued

Receptor-binding properties of PTH and PTHrP analogs
COS-7 cells transfected with plasmids encoding the human PTH/PTHrP receptor or the human PTH-2 receptor were stimulated with the indicated ligand for 1 h at room temperature, and the resulting levels of intracellular cAMP were quantified by RIA. The maximum values indicate the highest level of cAMP that was attained for each ligand with each receptor. The mean basal cAMP values (not subtracted) were $4.6 \pm 0.2$ and $5.4 \pm 0.3$ pmoles/well for the PTH/PTHrP and PTH-2 receptors, respectively. Data are the mean ($\pm$s.e.m.) of values obtained from the number of experiments indicated (n).

| | cAMP accumulation | | | | | |
|---|---|---|---|---|---|---|
| | PTH/PTHrP receptor | | | PTH-2 receptor | | |
| Ligand | EC50 (nM) | Maximum (pmoles/well) | (n) | EC50 (nM) | Maximum (pmoles/well) | (n) |
| [15, W23, Y36]hpTHrP-(1-36)NH2 | $0.21 \pm 0.06$ | $109 \pm 10$ | 4 | $0.5 \pm 0.3$ | $65 \pm 7$ | 4 |
| [H5,Y34]hPTH-(1-34)NH2 | $0.93 \pm 0.37$ | $116 \pm 19$ | 3 | >1000 | $10 \pm 1$ | 3 |
| [F23, Y34]hPTH-(1-34)NH2 | $0.23 \pm 0.02$ | $104 \pm 16$ | 4 | $7.6 \pm 2.2$ | $50 \pm 8$ | 4 |
| [H5, F23, Y34]hPTH-(1-34)NH2 | $1.18 \pm 0.29$ | $110 \pm 19$ | 3 | >1000 | $7.1 \pm 0.9$ | 3 |
| Hybrid-1 (SEQ ID NO: 3) | $0.23 \pm 0.04$ | $140 \pm 17$ | 3 | >1000 | $5.3 \pm 0.6$ | 3 |
| [Y34]hPTHrP-(1-34)/hPTH-(15-34)NH2 Hybrid-5 (SEQ ID NO: 4) | $0.43 \pm 0.16$ | $133 \pm 14$ | 3 | >1000 | $4.2 \pm 0.4$ | 3 |
| [Y34]hPTHrP-(1-18)/hPTH-(19-34)NH2 Hybrid-4 (SEQ ID NO: 5) | $0.27 \pm 0.06$ | $107 \pm 17$ | 4 | >1000 | $6.7 \pm 0.6$ | 4 |
| [Y34]hPTHrP-(1-21)/hPTH-(22-34)NH2 Hybrid-3 (SEQ ID NO: 6) | | | | | | |
| [Y34]hPTHrP-(1-23)/hPTH-(24-34)NH2 Hybrid-2 (SEQ ID NO: 7) | $0.42 \pm 0.13$ | $95 \pm 9$ | 4 | >1000 | $11 \pm 1$ | 4 |
| [Y34]hPTH-(1-14)/hPTHrP-(15-34)NH2 | $0.74 \pm 0.37$ | $123 \pm 28$ | 3 | $2.1 \pm 0.5$ | $58 \pm 12$ | 3 |

In replacement Table 2-continued, line 4, please delete "ofintracellular" and insert therefor -- of intracellular --.

Column 21,
Line 13, please delete "PTHrP of SEQ ID NO:2" and insert therefor -- PTHrP having the amino acid sequence of SEQ ID NO:2 --.

Column 22,
Line 12, please delete "PTHrP of SEQ ID NO:2" and therefor -- PTHrP having the amino acid sequence of SEQ ID NO:2 --.

Signed and Sealed this

Sixteenth Day of April, 2002

*Attest:*

JAMES E. ROGAN
*Director of the United States Patent and Trademark Office*

*Attesting Officer*

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 34 amino acids
      (B) TYPE: amino acid
      (C) STRANDEDNESS: single
      (D) TOPOLOGY: Not Relevant (ii) MOLECULE TYPE: peptide (ix) FEATURE:
      (A) NAME/KEY: MODIFIED-SITE
      (B) LOCATION: 34
      (C) OTHER INFORMATION: CARBOXY-TERMINAL MODIFICATION OF
          TYROSINE-AMIDE (xi) SEQUENCE DESCRIPTION: SEQ ID NO:1:

```
Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Tyr
```

(2) INFORMATION FOR SEQ ID NO:2:

(i) SEQUENCE CHARACTERISTICS:

-continued (A) LENGTH: 36 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 36
        (C) OTHER INFORMATION: CARBOXY-TERMINAL MODIFICATION OF
            TYROSINE-AMIDE (xi) SEQUENCE DESCRIPTION: SEQ ID NO:2:

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Tyr
        35

(2) INFORMATION FOR SEQ ID NO:3:

(i) SEQUENCE CHARACTERISTICS:
        (A) LENGTH: 34 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 34
        (C) OTHER INFORMATION: CARBOXY-TERMINAL MODIFICATION OF
            TYROSINE-AMIDE (xi) SEQUENCE DESCRIPTION: SEQ ID NO:3:

Ala Val Ser Glu His Gln Leu Leu His Asp Lys Gly Lys Ser Leu Asn
1               5                   10                  15

Ser Met Glu Arg Val Glu Trp Leu Arg Lys Lys Leu Gln Asp Val His
            20                  25                  30

Asn Tyr (2) INFORMATION FOR SEQ ID NO:4:

(i) SEQUENCE CHARACTERISTICS:
        (A) LENGTH: 34 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 34
        (C) OTHER INFORMATION: CARBOXY-TERMINAL MODIFICATION OF
            TYROSINE-AMIDE (xi) SEQUENCE DESCRIPTION: SEQ ID NO:4:

Ala Val Ser Glu His Gln Leu Leu His Asp Lys Gly Lys Ser Ile Gln
1               5                   10                  15

Asp Leu Glu Arg Val Glu Trp Leu Arg Lys Lys Leu Gln Asp Val His
            20                  25                  30

Asn Tyr (2) INFORMATION FOR SEQ ID NO:5:

(i) SEQUENCE CHARACTERISTICS:
        (A) LENGTH: 34 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 34
        (C) OTHER INFORMATION: CARBOXY-TERMINAL MODIFICATION OF
            TYROSINE-AMIDE (xi) SEQUENCE DESCRIPTION: SEQ ID NO:5:

Ala Val Ser Glu His Gln Leu Leu His Asp Lys Gly Lys Ser Ile Gln
1               5                   10                  15

Asp Leu Arg Arg Arg Glu Trp Leu Arg Lys Lys Leu Gln Asp Val His
            20                  25                  30

Asn Tyr (2) INFORMATION FOR SEQ ID NO:6:

(i) SEQUENCE CHARACTERISTICS:
        (A) LENGTH: 34 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 34
        (C) OTHER INFORMATION: CARBOXY-TERMINAL MODIFICATION OF
            TYROSINE-AMIDE (xi) SEQUENCE DESCRIPTION: SEQ ID NO:6:

Ala Val Ser Glu His Gln Leu Leu His Asp Lys Gly Lys Ser Ile Gln
1               5                   10                  15

Asp Leu Arg Arg Arg Phe Phe Leu Arg Lys Lys Leu Gln Asp Val His
            20                  25                  30

Asn Tyr (2) INFORMATION FOR SEQ ID NO:7:

(i) SEQUENCE CHARACTERISTICS:
        (A) LENGTH: 34 amino acids
        (B) TYPE: amino acid
        (C) STRANDEDNESS: single
        (D) TOPOLOGY: Not Relevant (ii) MOLECULE TYPE: peptide (ix) FEATURE:
        (A) NAME/KEY: MODIFIED-SITE
        (B) LOCATION: 34
        (C) OTHER INFORMATION: CARBOXY-TERMINAL MODIFICATION OF
            TYROSINE-AMIDE (xi) SEQUENCE DESCRIPTION: SEQ ID NO:7:

-continued

```
Ser Val Ser Glu Ile Gln Leu Met His Asn Leu Gly Lys His Ile Gln
1               5                   10                  15

Asp Leu Arg Arg Arg Phe Phe Leu His His Leu Ile Ala Glu Ile His
                20                  25                  30

Thr Tyr
```